US008350905B2

(12) United States Patent
Yamada

(10) Patent No.: US 8,350,905 B2
(45) Date of Patent: Jan. 8, 2013

(54) MICROSCOPE SYSTEM, IMAGE GENERATING METHOD, AND PROGRAM FOR PRACTICING THE SAME

(75) Inventor: Tatsuki Yamada, Hachioji (JP)

(73) Assignee: Olympus Corporation, Tokyo (JP)

( * ) Notice: Subject to any disclaimer, the term of this patent is extended or adjusted under 35 U.S.C. 154(b) by 818 days.

(21) Appl. No.: 12/357,059

(22) Filed: Jan. 21, 2009

(65) Prior Publication Data
US 2009/0213214 A1 Aug. 27, 2009

(30) Foreign Application Priority Data
Jan. 23, 2008 (JP) ................... 2008-012651

(51) Int. Cl.
H04N 7/18 (2006.01)
G06K 9/00 (2006.01)

(52) U.S. Cl. ............ 348/80; 348/79; 348/254; 382/128; 382/133; 250/306; 250/310; 250/309; 250/580; 359/363; 359/379; 359/368; 359/857; 359/867

(58) Field of Classification Search .................... 348/79, 348/80
See application file for complete search history.

(56) References Cited

U.S. PATENT DOCUMENTS

| 6,002,527 | A  | * | 12/1999 | Ohtake ......................... 359/683 |
| 6,272,235 | B1 | * | 8/2001  | Bacus et al. ................... 382/133 |
| 6,418,236 | B1 | * | 7/2002  | Ellis et al. ..................... 382/128 |
| 6,920,239 | B2 | * | 7/2005  | Douglass et al. .............. 382/128 |
| 7,016,109 | B2 | * | 3/2006  | Nakagawa ..................... 359/380 |
| 7,027,627 | B2 | * | 4/2006  | Levin et al. ................... 382/128 |
| 7,133,545 | B2 | * | 11/2006 | Douglass et al. .............. 382/128 |
| 7,756,357 | B2 | * | 7/2010  | Yoneyama ..................... 382/280 |
| 7,932,504 | B2 | * | 4/2011  | Yamada ....................... 250/461.2 |
| 2004/0105000 | A1 | * | 6/2004 | Yuri .................................. 348/79 |
| 2005/0002587 | A1 | * | 1/2005 | Yoneyama ..................... 382/254 |
| 2009/0175417 | A1 |   | 7/2009 | Sasano |

FOREIGN PATENT DOCUMENTS

| JP | 06-281866 | 10/1994 |
| JP | 09-281405 | 10/1997 |
| JP | 2000-039566 | 2/2000 |
| JP | 2002-202463 | 7/2002 |
| JP | 2002-258163 | 9/2002 |
| JP | 2004-286666 | 10/2004 |
| JP | 2005-345310 | 12/2005 |
| JP | 2006-343573 | 12/2006 |
| WO | 9720198 | 6/1997 |
| WO | WO 97/20198 | 6/1997 |
| WO | 9844446 | 10/1998 |
| WO | WO 02/37158 A3 | 5/2002 |

* cited by examiner

Primary Examiner — Jude Jean Gilles

(57) ABSTRACT

A microscope system has a VS image generation means for generating a virtual slide image of a specimen which is constructed by mutually connecting a plurality of microscope images with a first photomagnification photographed and acquired whenever an objective lens and the specimen are relatively moved in a direction perpendicular to the optical axis and which represents the entire image of the specimen, an object-of-interest set means setting an object of interest with respect to the entire image of the specimen represented by the VS image, and a three-dimensional VS image generation means for generating a three-dimensional VS image which is constructed by connecting the microscope images at different focal positions in accordance with the same focal position and which is constructed from the microscope images with a second photomagnification higher than the first photomagnification and represents the image of the object of interest.

15 Claims, 31 Drawing Sheets

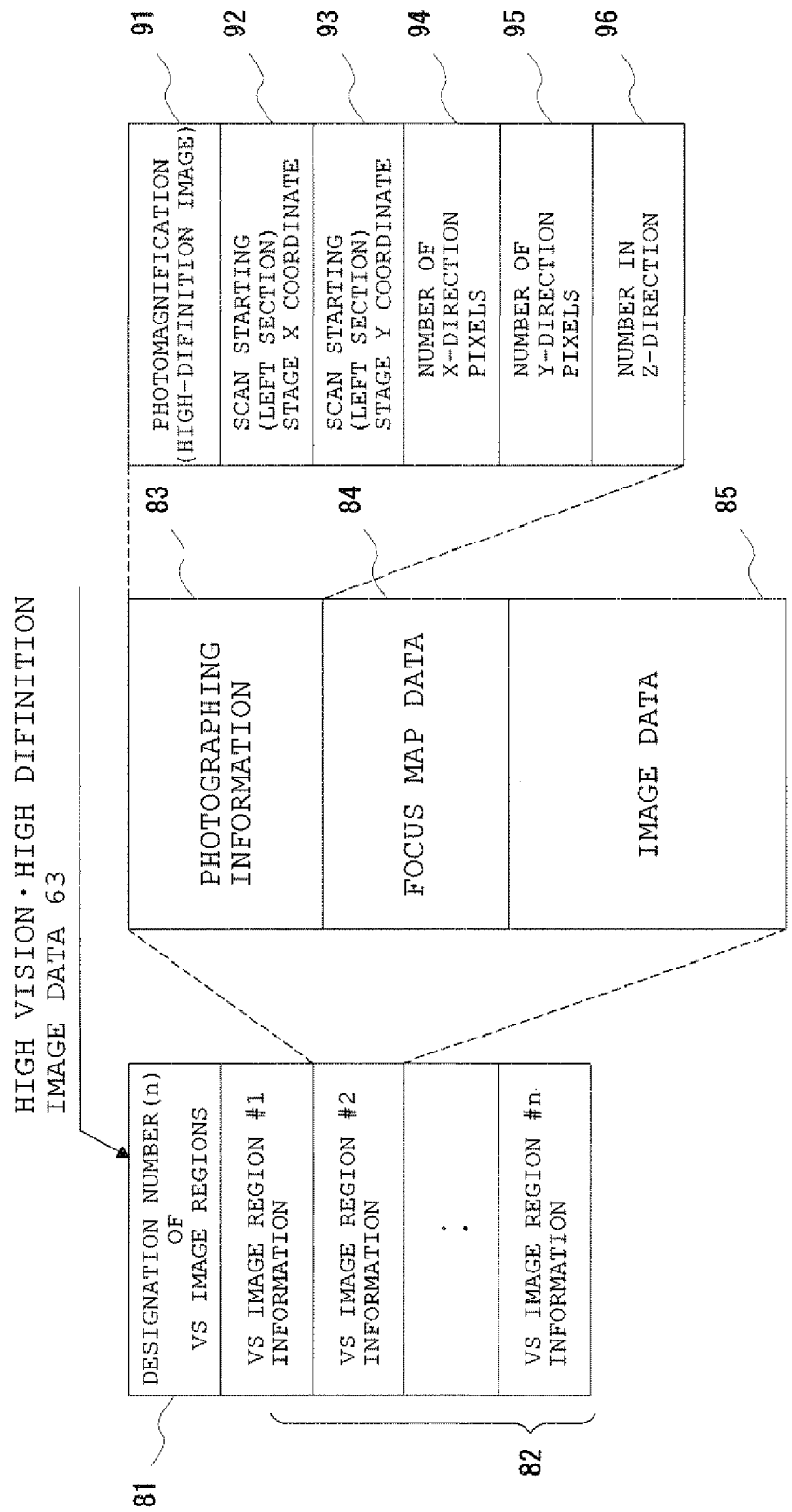

FIG. 8A

| 131 | 132 BOUNDING BOX | | | | 133 CENTER OF GRAVITY | | 134 AREA | 135 PERIMETER | 136 ROUNDNESS | 137 MAJOR DIAMETER | 138 MINOR DIAMETER | 139 ASPECT RATIO | 141 NUMBER OF NUCLEUS | 142 NUCLEUS AREA | 143 NUCLEUS DISPERSION | 144 NUCLEUS LUMINANCE | 145 N/C RATIO | 146 CYTOPLASM LUMINANCE | 147 DETERMINATION | | 148 IMAGE ID | 149 CONFIRMED FLAG |
|---|---|---|---|---|---|---|---|---|---|---|---|---|---|---|---|---|---|---|---|---|---|---|
| LABEL | X | Y | W | H | X | Y | | | | | | | | | | | | | CLASS 147a | SCORE 147b | | |
| | | | | | | | | | | | | | | | | | | | | | | |
| | | | | | | | | | | | | | | | | | | | | | | |
| | | | | | | | | | | | | | | | | | | | | | | |

| LABEL | BOUNDING BOX | | | | CENTER OF GRAVITY | | AREA | PERIMETER | ROUNDNESS | MAJOR DIAMETER | MINOR DIAMETER | ASPECT RATIO |
|---|---|---|---|---|---|---|---|---|---|---|---|---|
| | X | Y | W | H | X | Y | | | | | | |
| 1 | | | | | | | | | | | | |
| 2 | | | | | | | | | | | | |
| 3 | | | | | | | | | | | | |
| | | | | | | | | | | | | |
| | | | | | | | | | | | | |
| | | | | | | | | | | | | |
| | | | | | | | | | | | | |

FIG.13A

| | III | IIb | I | IIa |
|---|---|---|---|---|
| N/C RATIO | HIGH | BOUNDARY | AVERAGE | LOW |
| AREA OF NUCLEUS | LARGE | BOUNDARY | AVERAGE | SMALL |
| LUMINANCE OF NUCLEUS | DARK | BOUNDARY | AVERAGE | BRIGHT |
| LUMINANCE OF CYTOPLASM | DARK | BOUNDARY | AVERAGE | BRIGHT |

FIG.13B

| ITEM | | | | DETERMINATION RESULT | |
|---|---|---|---|---|---|
| N/C RATIO | LUMINANCE OF NUCLEUS | AREA OF NUCLEUS | LUMINANCE OF CYTOPLASM | CLASS | SCORE |
| I | I | I | I | NORMAL | 0 |
| I | I | I | IIa | NORMAL | 0 |
| I | I | I | IIb | NORMAL | 0 |
| I | I | I | III | NORMAL | 0 |
| . | . | . | . | . | . |
| . | . | . | . | . | . |
| III | III | III | IIb | ABNORMAL | 10 |
| III | III | III | III | ABNORMAL | 10 |

FIG.13C

| | III | IIb | I | IIa |
|---|---|---|---|---|
| N/C RATIO | HIGH | BOUNDARY | AVERAGE | LOW |
| AREA OF NUCLEUS | LARGE | BOUNDARY | AVERAGE | SMALL |
| LUMINANCE OF NUCLEUS | DARK | BOUNDARY | AVERAGE | BRIGHT |
| DISPERSION OF NUCLEUS | HIGH | BOUNDARY | AVERAGE | LOW |

FIG.13D

| ITEM | | | | DETERMINATION RESULT | |
|---|---|---|---|---|---|
| N/C RATIO | LUMINANCE OF NUCLEUS | AREA OF NUCLEUS | DISPERSION OF NUCLEUS | CLASS | SCORE |
| I | I | I | I | NORMAL | 0 |
| I | I | I | IIa | NORMAL | 0 |
| I | I | I | IIb | NORMAL | 0 |
| I | I | I | III | NORMAL | 0 |
| . | . | . | . | . | . |
| . | . | . | . | . | . |
| III | III | III | IIb | ABNORMAL | 10 |
| III | III | III | III | ABNORMAL | 10 |

| ITEM | | | | DETERMINATION RESULT | | NEED FLAG OF DETAIL IMAGE |
|---|---|---|---|---|---|---|
| N/C RATIO | LUMINANCE OF NUCLEUS | AREA OF NUCLEUS | LUMINANCE OF CYTOPLASM | CLASS | SCORE | |
| I | I | I | I | NORMAL | 0 | NOT NEED |
| I | I | I | IIa | NORMAL | 0 | NOT NEED |
| I | I | I | IIb | NORMAL | 0 | NOT NEED |
| I | I | I | III | NORMAL | 0 | NOT NEED |
| . | . | . | . | . | . | . |
| . | . | . | . | . | . | . |
| III | III | III | IIb | ABNORMAL | 10 | NEED |
| III | III | III | III | ABNORMAL | 10 | NEED |

| ITEM | | | | DETERMINATION RESULT | | NEED FLAG OF DETAIL IMAGE |
|---|---|---|---|---|---|---|
| N/C RATIO | LUMINANCE OF NUCLEUS | AREA OF NUCLEUS | LUMINANCE OF CYTOPLASM | CLASS | SCORE | |
| I | I | I | I | NORMAL | 0 | NOT NEED |
| I | I | I | IIa | NORMAL | 0 | NOT NEED |
| I | I | I | IIb | NORMAL | 0 | NOT NEED |
| I | I | I | III | NORMAL | 0 | NOT NEED |
| . | . | . | . | . | . | . |
| . | . | . | . | . | . | . |
| III | III | III | IIb | ABNORMAL | 10 | NEED |
| III | III | III | III | ABNORMAL | 10 | NEED |

FIG.17C

| LABEL | | DETERMINATION 147 | | IMAGE ID 148 | CONFIRMED FLAG 149 | NEED FLAG OF DETAIL IMAGE 381 |
|---|---|---|---|---|---|---|
| | | CLASS | SCORE | | | |
| 1 | | | | | | |
| 2 | | | | | | |
| 3 | | | | | | |
| | | | | | | |
| | | | | | | |
| | | | | | | |

| EVALUATION VALUE | EVALUATION CONTENTS |
|---|---|
| 0 | NORMAL |
| 1 | LOW-LEVEL HYPER-METAMORPHOSIS |
| 2 | MIDDLE-LEVEL HYPER-METAMORPHOSIS |
| 3 | HIGH-LEVEL HYPER-METAMORPHOSIS |
| 4 | CANCER WITHIN EPITHELIUM |
| 5 | INFILTRATION CANCER |
| 9 | DETERMINATION IMPOSSIBLE |

FIG. 21

| LABEL | EVALUATION VALUE | COMMENT |
|---|---|---|
| | | |
| | | |
| | | |
| | | |
| | | |
| | | |

MICROSCOPE SYSTEM, IMAGE GENERATING METHOD, AND PROGRAM FOR PRACTICING THE SAME

This application claims benefits of Japanese Patent Application No. 2008-012651 filed in Japan on Jan. 23, 2008, the contents of which are incorporated herein by reference.

BACKGROUND OF THE INVENTION

1. Field of the Invention

This invention relates to microscope technology and in particular, to the technology of a microscope system suitable for use in cytology in which a microscope is used to make the record and/or observation of a high-vision and high-definition microscope image.

2. Description of Related Art

In general, the cytologic diagnosis is made, for example, as follows.

First, a cytotechnologist uses an objective lens with relative low (for example, 10×) magnification to perform the screening of the entire specimen and prosecutes the search of a malignant cell or an exceptional cell (such a cell is called an "abnormal cell" in the present invention). Here, when a suspectable cell has been found, the objective lens is replaced with that of high (for example, 40×) magnification in order to observe the structure of the cell in more detail, and a detailed observation is carried out while changing the focal position to ascertain whether it is a target cell. Here, in the case where the cell of a target or abnormality has been found, a mark is put with ink on a slide glass on which the specimen is smeared. Also, for a positive case and/or a false positive case, a cytologic specialist or instructor performs re-microscopy to make a final determination and reports examination results under his signature to a client. On the other hand, when the cytotechnologist has made the determination of a negative case, the examination results are reported to the client, without checking of the cytologic specialist and/or instructor, in most cases.

It is very laborious work to screen a malignant cell from among a great number of cells. The occurrence of a false negative case caused by an oversight for the malignant cell attributable to the fatigue and ability of the cytotechnologist offers a problem. A determination made as to whether a screened cell is abnormal or not depends on the ability and/or experience of the cytotechnologist, and thus there is also the problem that variations are caused to examination accuracy. In consideration of such problems, the technique is known that the accuracy of a cytologic examination is improved in such a way that the screening of the abnormal cell is carried out by a machine and the determination of benignancy or malignancy, such as "malignant" or "malignancy suspected", is made by the cytotechnologist. For such a technique, for example, Japanese Patent Publication No. 2000-501184 discloses an apparatus in which a specimen is scanned at a low magnification, an abnormal cell is automatically extracted in accordance with the geometry of a nucleus, the region of an extracted cell is photographed at a high magnification to store its image, and thereby the extracted abnormal cell can be evaluated in accordance with the image by a pathologist.

Further, for example, Japanese Patent Publication No. 2004-517349 discloses an apparatus in which the X and Y coordinates of an abnormal cell automatically extracted by specimen scanning are recorded and the coordinates are reproduced under a microscope (a review station) provided with a motorized stage so that the abnormal cell can be observed.

On the other hand, a system is known that whenever the motorized stage is utilized to move the visual field (that is, whenever the objective lens and the specimen are relatively moved in a direction perpendicular to the optical axis of the microscope), a plurality of microscope images of the specimen are photographed and acquired, these are mutually connected, and thereby a wide-vision and high-resolution microscope image is constructed and utilized for a pathological diagnosis, etc. In the present invention, it is assumed that this microscope image is referred to as a "VS (virtual slide) image", and a system producing the VS image in this way is termed a "virtual slide microscope system".

For the technology of the virtual slide microscope system, for example, Japanese Patent Kokai No. 2006-343573 discloses a system automatically producing a three-dimensional VS image, and it is possible to use this system for the cytologic examination. In addition, Kokai No. 2006-343573 discloses the technique that after the examination undergone by the use of the system is completed, only a region of interest designated by a pathologist is held with high-definition and three-dimensional information and other regions are held by reducing the number of dimensions to two dimensions (a plane) and also by lowering the resolution, and thereby the storage capacity of a memory is saved.

Japanese Patent Kokai No. Hei 9-281405 also discloses the virtual slide microscope system. As for the rest, with respect to the present invention, for example, "Digital Image Processing", the supervision of Digital Image Processing Editorial Committee, Second Edition, Computer Graphic Arts Society, Mar. 1, 2007, pp. 108-110 and pp. 177-184, sets forth the explanation of various well-known digital image processing techniques, for example, of smoothing filter processing of the Gaussian filter, contour tracking for finding the boundary between pixel connecting components relative to a binary image, closing processing by dilation and erosion for eliminating a small hole in the image, labeling processing for distinguishing by attaching different labels to different pixel connecting components, and calculation processing of the geometric feature parameter digitizing the feature of the geometry of the pixel connecting component.

SUMMARY OF THE INVENTION

The microscope system according to the present invention has an (entire specimen VS) image generation means generating a VS image of the entire specimen which is a virtual slide image (a VS image) of a specimen constructed by mutually connecting a plurality of microscope images photographed and acquired whenever an objective lens and the specimen are relatively moved in a direction perpendicular to the optical axis and which is constructed from the microscope images with a first photomagnification and represents the entire image of the specimen; an object-of-interest set means setting an object of interest with respect to the entire image of the specimen represented by the entire specimen VS image; and an (object-of-interest three-dimensional VS) image generation means generating an object-of-interest three-dimensional VS image which is a three-dimensional VS image constructed by connecting the microscope images at different focal positions in accordance with the same focal position and which is constructed from the microscope images with a second photomagnification higher than the first photomagnification and represents the image of the object of interest.

Also, in the microscope system according to the present invention described above, the object-of-interest set means can be constructed so that a region representing the image of an abnormal cell, of cells constituting the specimen in the entire specimen VS image, is set as the object of interest.

Also, in this case, the object-of-interest set means can be constructed so that whether the cell is abnormal is determined on the basis of one of the geometric feature parameter relative to the image of the cell represented by the entire specimen VS image and the image feature parameter relative to the image of the cell.

Also, in this case, the object-of-interest set means can be constructed so that whether the cell is abnormal or not is determined on the basis of the areas of images of a nucleus and cytoplasm constituting the cell in the entire specimen VS image and the luminances of images of the nucleus and cytoplasm.

Also, in this case, the object-of-interest set means can be constructed so that, on the basis of color space components of pixels constituting the image of the cell in the entire specimen VS image, which of images of the nucleus and cytoplasm is constructed with the pixels is determined.

The microscope system according to the present invention mentioned above can be designed to further have an object-of-interest three-dimensional VS image display means displaying the object-of-interest three-dimensional VS images in a preset order when a plurality of object of interest are set.

Also, in this case, the object-of-interest set means can be constructed so that a region representing the image of an abnormal cell, of cells constituting the specimen in the entire specimen VS image, is set as the object of interest and the object-of-interest three-dimensional VS image display means can be constructed so that the object-of-interest three-dimensional VS images relative to the object of interest are displayed in order of increasing abnormality of abnormal cells represented by the object of interest.

Alternatively, in this case, the object-of-interest set means can be constructed so that the extent of the abnormality of the cell is determined on the basis of one of the geometric feature parameter relative to the image of the cell represented by the entire specimen VS image and the image feature parameter relative to the image of the cell, and the VS image display means can be constructed so that the three-dimensional VS images relative to the object of interest are displayed in order according to the extent of the abnormality of the cell determined by the object-of-interest set means.

Also, in this case, the object-of-interest set means can be constructed so that the extent of the abnormality of the cell is determined on the basis of the areas of images of a nucleus and cytoplasm constituting the cell in the entire specimen VS image and the luminances of images of the nucleus and cytoplasm.

In the microscope system according to the present invention mentioned above, the object-of-interest set means can be constructed so that whether the cell determined to be abnormal on the basis of the entire specimen VS image is abnormal or not is secondarily determined in accordance with a plurality of microscope images with high magnification at different focal positions which are microscope images with higher magnification than the first photomagnification relative to the cell, and a region representing a cell determined to be normal by this secondary determination is excluded from the setting of the object of interest.

Also, in this case, the object-of-interest set means can be constructed so that when the existence of the nucleus superimposed on the image of the cell determined to be abnormal because of a large area of the image of the nucleus in the entire specimen VS image is recognized on the basis of the microscope image with high magnification, the image on which the nucleus is superimposed is excluded from a criterion, as the secondary determination, to determine whether the cell is abnormal or not.

The microscope system according to present invention described above can be designed to further have a VS image generation control means controlling whether the generation of the three-dimensional VS image relative to the object of interest set by the object-of-interest set means is performed by the three-dimensional VS image generation means on the basis of the extent of the abnormality of the abnormal cell represented by the object of interest.

The microscope system according to present invention described above can be designed to further have a VS image generation control means controlling whether the generation of the three-dimensional VS image relative to the object of interest set by the object-of-interest set means is performed by the three-dimensional VS image generation means on the basis of the image of another cell lying within a preset distance from the abnormal cell represented by the object of interest.

The microscope system according to present invention described above can be designed to further have an evaluation value acquirement means acquiring the input of an evaluation value relative to the object of interest, and also to have a display need determination means in which a determination is made on the basis of the evaluation value relative to the object of interest as to whether the display of the object-of-interest three-dimensional VS image relative to the object of interest is required and a VS image display means displaying the object-of-interest three-dimensional VS image determined by the display need determination means to need the display.

The image generating method of another aspect of the present invention is such that a first VS image generation means generates the VS image which is a virtual slide image (a VS image) of a specimen constructed by mutually connecting a plurality of microscope images photographed and acquired whenever an objective lens and the specimen are relatively moved in a direction perpendicular to the optical axis and which is constructed from the microscope images with a first photomagnification and represents the entire image of the specimen; an object-of-interest set means sets the object of interest with respect to the entire image of the specimen represented by the entire specimen VS image; and a second VS image generation means generates an object-of-interest three-dimensional VS image which is a three-dimensional VS image constructed by connecting the microscope images at different focal positions in accordance with the same focal position and which is constructed from the microscope images with a second photomagnification higher than the first photomagnification and represents the image of the object of interest.

The program of a further aspect of the present invention contains a non-transitory computer readable medium having a comauter readable) o ram code embodied therein said con u er readable ro rram code ada ted to be executed to im.lemcnt a method for generating a report, said method comprises a computer that executes a process generating the VS image which is a virtual slide image (a VS image) of a specimen constructed by mutually connecting a plurality of microscope images photographed and acquired whenever an objective lens and the specimen are relatively moved in a direction perpendicular to the optical axis and which is constructed from the microscope images with a first photomagnification and represents the entire image of the specimen, a process setting an object of interest with respect to the entire image of the specimen represented by the entire specimen VS image, and a process generating a three-dimensional VS image which is a three-dimensional VS image constructed by connecting the microscope images at different focal positions in accordance with the same focal position and which is constructed from the microscope images with a second photomagnification higher than the first photomagnification and represents the image of the object of interest.

According to the present invention, by the above construction, it is possible that the accuracy and efficiency of the cytologic examination are both improved in the virtual slide microscope system.

These and other features and advantages of the present invention will become apparent from the following detailed description of the preferred embodiments when taken in conjunction with the accompanying drawings.

BRIEF DESCRIPTION OF THE DRAWINGS

FIG. 6C is a view showing the structure of wide-vision and high-definition image data.

FIG. 8A is a view showing an example of a cell region map table.

FIG. 12D is a view showing an example of a nucleus region map table.

FIG. 13A is a view showing a table in which items used for the abnormality determination of a solitary scattered cell and its abnormality levels are listed.

FIG. 13B is a view showing a determination table used for the abnormality determination of the solitary scattered cell.

FIG. 13C is a view showing a table in which items used for the abnormality determination of a cell mass and their abnormality levels are listed.

FIG. 13D is a view showing a determination table used for the abnormality determination of the cell mass.

FIG. 17A is a view showing an example of an abnormality determination table of isolated and scattered cells in which the determination on the need for a detailed image is also possible.

FIG. 17B is a view showing an example of an abnormality determination table of the cell mass in which the determination on the need for a detail image is also possible.

FIG. 17C is a view showing an example of the cell region map table in which the determination on the need for a detail image is also possible.

FIG. 20 is a view showing an example of a corresponding table of the numerical values and details of the evaluation of the abnormal cell.

FIG. 21 is a view showing an example of an observation data table.

DETAILED DESCRIPTION OF THE PREFERRED EMBODIMENTS

In accordance with the drawings, the embodiments of the present invention will be explained below.

Figure 1:
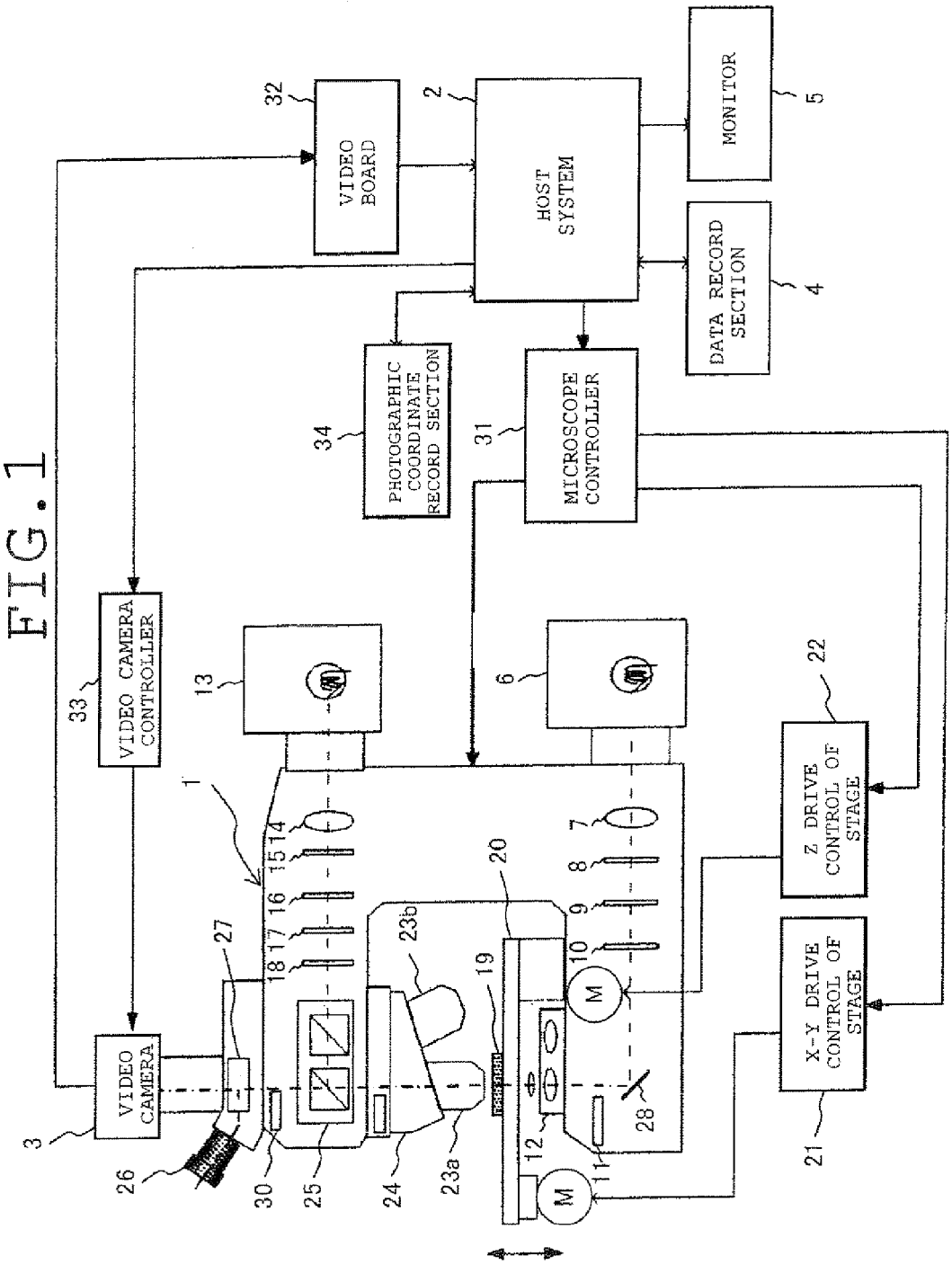
FIG. 1 is a view showing the structure of a virtual slide microscope system for carrying out the present invention.

FIG. 1 shows the structure of the virtual slide microscope system for carrying out the present invention. In the system of FIG. 1, a microscope apparatus 1 includes a transmitting illumination light source 6, a collector lens 7 collecting illumination light of the transmitting illumination light source 6, a filter unit 8 for transmission, a transmission field stop 9, a transmission aperture stop 10, a condenser optical element unit 11, and a top lens unit 12, as a transmitting observation optical system. The microscope apparatus 1 further includes a reflecting illumination light source 13, a collector lens 14 collecting illumination light of the reflecting illumination light source 13, a filter unit 15 for reflection, a reflection shutter 16, a reflection field stop 17, and a reflection aperture stop 18, as a reflecting observation optical system.

On an observation optical path that the optical path of the transmitting observation optical system is superimposed on that of the reflecting observation optical system, a motorized stage 20 on which a specimen is placed is provided. The motorized stage 20 can be moved in directions parallel and perpendicular to the optical axis, and the control of this movement is made by a stage X-Y drive control section 21 and a stage Z drive control section 22. Also, the motorized stage 20 has an original position detecting function by an origin sensor (not shown) and coordinates can be set with respect to individual parts of the specimen 19 placed on the motorized stage 20. Also, in the embodiments, it is assumed that the transmitting observation optical system of the microscope apparatus 1 is used to carry out the observation of the specimen 19.

On the observation optical path of the microscope apparatus 1 are provided a revolver 24 mounted with a plurality of objective lenses 23*a*, 23*b*, . . . (which are hereinafter generically referred to as an "objective lens 23" according to the need) to select the objective lens 23 used for the observation in this case through a rotating operation; a cube unit 25 switching microscopy; and a beam splitter 27 splitting the observation optical path into two sides, an eyepiece 26 and a video camera 3. When the motorized stage 20 on which the specimen 19 is placed is moved in the direction perpendicular to the optical axis, the objective lens 23 and the specimen 19 are relatively moved to make a right angle with the optical axis.

A polarizer 28, a DIC (differential interference contrast) prism, not shown, and an analyzer 30, which are provided for a differential interference observation, are such that they can be introduced into the observation optical path according to the need. Also, these units are not used in the embodiments. A microscope controller 31 connected to a host system 2 has the function of controlling the operation of the entire microscope apparatus 1. The microscope controller 31 executes the control of the units, such as a change of the objective lens 23 and the adjustment of the transmitting illumination light source 6. The microscope controller 31 also has the function of detecting a present condition of each unit in the microscope apparatus 1 to feed this detection result to the host system 2. In addition, the microscope controller 31 is also connected to the stage X-Y drive control section 21 and the stage Z drive control section 22, and the host system 2 is also capable of performing the control of the motorized stage 20 through the microscope controller 31.

The microscope image of the specimen 19 (an observation body) picked up by a CCD (charged coupled device) that is an image sensor in the video camera 3 is brought into the host system 2 through a video board 32. The host system 2 is capable of performing the ON/OFF operation of automatic gain control, the gain setting, the ON/OFF operation of automatic exposure control, and the setting of exposure time with respect to the video camera 3 through a video camera controller 33. The host system 2 is also capable of storing the microscope image of the specimen 19 fed from the video camera 3, as an image data file, into a data record section 4. The data record section 4 corresponds to, for example, a hard disk unit or a mass storage. In the host system 2, for example, the image data recorded by the data record section 4 are read out in accordance with the instructions from a user so that the microscope image represented by the image data can be displayed on a monitor 5 that is a display section.

Moreover, the host system 2 has a so-called video AF (auto focus) function of performing a focusing operation in accordance with the contrast of the image formed by the video camera 3 and a function of recording the coordinates of a focusing position obtained by the video AF function in a photographing coordinate record section 34. Also, the host system 2 is s computer constructed as an ordinary standard and has an MPU (micro processing unit) in which the operation control of the entire microscope system is governed by the execution of a control program; a main memory used as a work memory by the MPU according to the need; an input section for acquiring various instructions from the user, such as a mouse or a keyboard; an interface unit managing the reception of various data among individual components of the microscope system; and an auxiliary storage unit, such as the hard disk unit, storing various programs and data. The host system 2 is such that a preset application program stored in the auxiliary storage unit is read out on the main memory and executed by the MPU, and thereby various processes described later are realized. Also, there are cases that, in these processes, the host system 2 feeds the control signal to the microscope controller 31 and causes the microscope controller 31 to perform, for example, the control of movement of the motorized stage 20, the control of the units of the microscope apparatus 1 in the change of the objective lens, and the detection of the conditions of the units, described above. However, in the following, the description of such operations is omitted.

An embodiment concerning the operation that the virtual slide microscope system shown in FIG. 1 produces the entire specimen VS image 19 (which is hereinafter referred to as an "entire specimen VS image") will be explained below with reference to FIGS. 2-6. Also, in this embodiment, the cell diagnosis specimen of cervix is used as the specimen 19, which is to use a specimen with Papanicolaou smear produced by liquid based cytology, for example, of a THINPREP (registered trademark) specimen made by Cytyc Corporation in which overlapping of cells when smeared on the slide glass is little (what is called a thin layer specimen) and the background unnecessary for the cytologic examination, such as blood or mucus, can be eliminated. Also, since processing itself for generating the entire specimen VS image is well known and its details are also described in Kokai Nos. 2006-343573 and Hei 9-381405 filed by the present applicant, it is briefly explained here.

The embodiments of the present invention using the virtual slide microscope system shown in FIG. 1 will be explained below.

Embodiment 1

[Generation of Entire Specimen VS Image]

Figure 2:
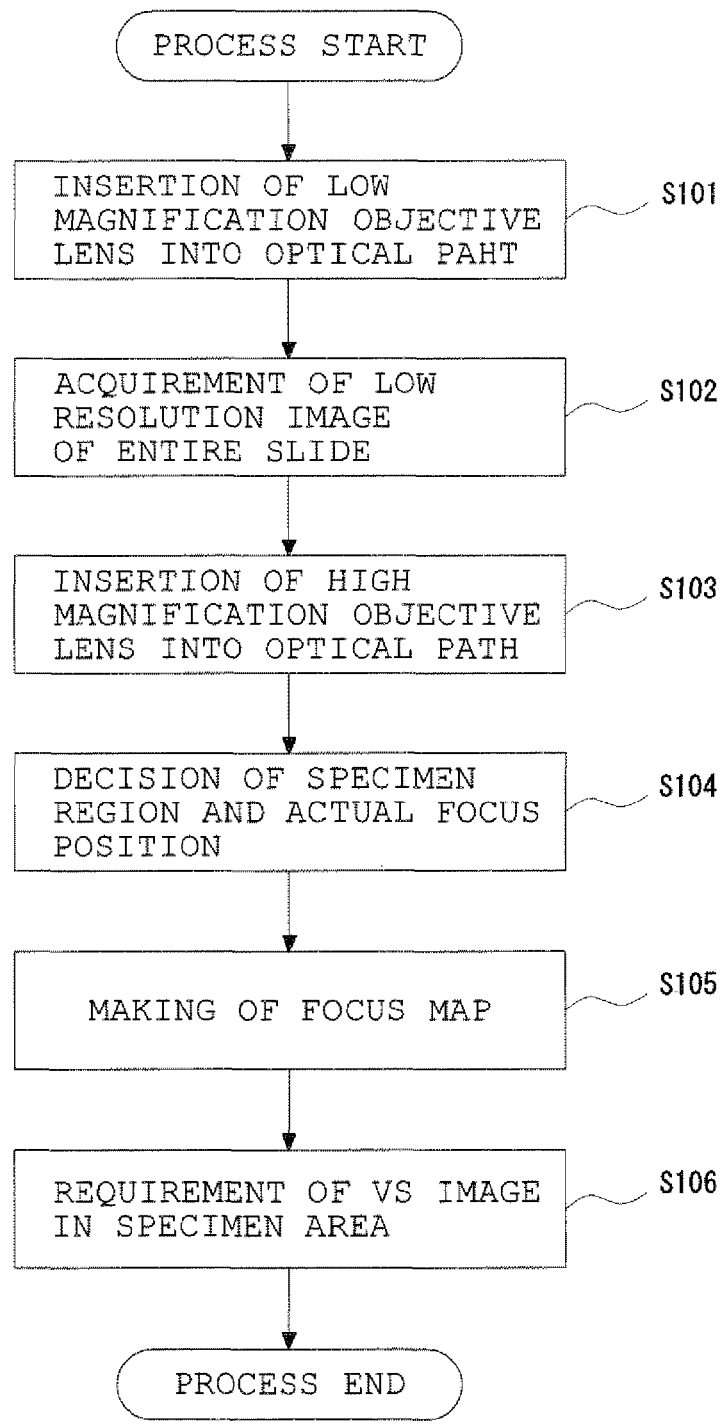
FIG. 2 is a flow chart showing the details of VS image generation processing of the entire specimen.
Figure 3:
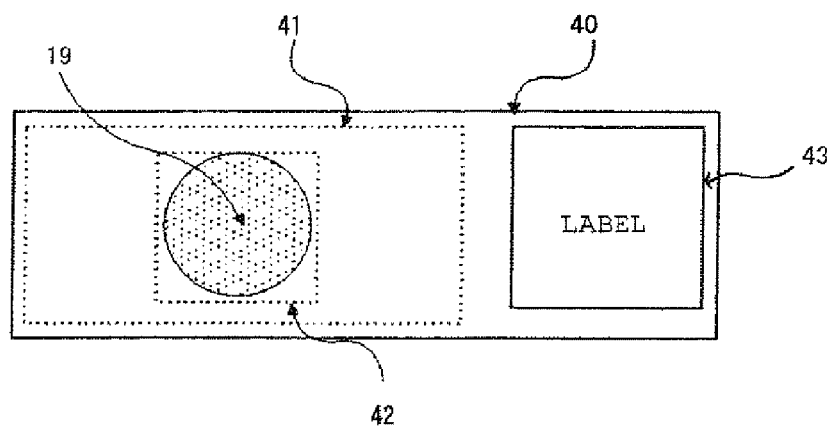
FIG. 3 is a view showing an example of a slide glass specimen.
Figure 4:
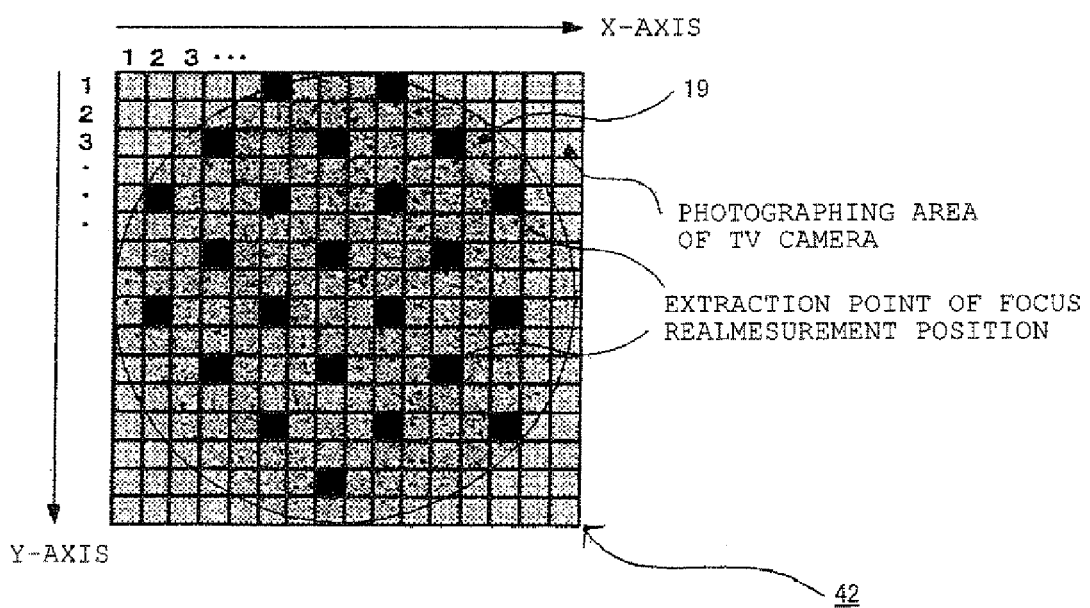
FIG. 4 is a view showing a state where the image of the entire specimen region is divided into a large number of small sections.
Figure 5:
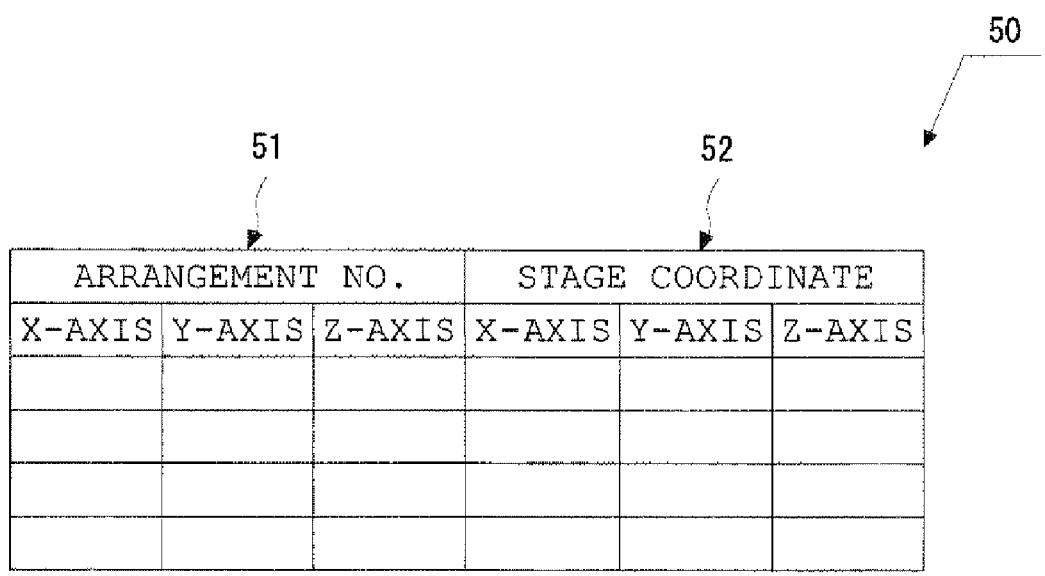
FIG. 5 is a view showing an example of the data structure of a focus map.

FIG. 2 is a flow chart showing the details of generation processing of the entire specimen VS image. FIG. 3 shows an example of a slide glass specimen (where the specimen 19 is placed on a slide glass 40). Also, although only the specimen 19 is shown in FIG. 1, the slide glass specimen is actually set on the motorized stage 20. FIG. 4 shows a state where the image of the entire specimen region is divided into a large number of small sections in order to produce a focus map. FIG. 5 shows an example of the data structure of the focus map.

In accordance with the flow chart of FIG. 2, the details of generation processing of the entire specimen VS image will be explained. First, in Step S101 of FIG. 2, in order to control the revolver 24 and confirm the presence of the specimen 19, a process that, for example, the objective lens 23 with 40× magnification is introduced into the optical path is executed. Next, in Step S102, a preset specimen search area 41 (for example, 25 mm vertical by 50 mm horizontal) on the slide glass 40 shown in FIG. 3 is divided into a plurality of sections in accordance with a photographic region width projected on the video camera 3 (that is, in accordance with the magnification of the objective lens 23 introduced into the optical path in Step S101) and the motorized stage 20 is moved in the X and Y directions to execute a process that the microscope image of each section obtained by the division is acquired by the video camera 3. A plurality of microscope images obtained by this process are mutually connected and thereby the entire slide image (the image of the whole of the specimen search area 41 in FIG. 3) is generated and is stored as the image file of the entire slide image in the data record section 4. Also, the movement of the motorized stage 20 in the X and Y directions means the movement of the motorized stage 20 on a plane perpendicular to the optical axis of the microscope apparatus 1. The control of the movement of the motorized stage 20 is performed by the stage X-Y drive control section 21. The specimen search area 41 refers to a preset, arbitrary region on the slide glass 40 and the specimen 19 is always placed in the specimen search area 41. Also, as shown in FIG. 3, a region in which a label 43 is applied on the slide glass 40 is likewise predetermined.

In Step S103, the revolver 24 is controlled and the objective lens 23 with higher (for example, 40×) magnification than that used in Step S101, predetermined (or indicated by the operation of an operator), is introduced into the optical path. The changeover of the objective lens 23 is performed to construct the entire specimen VS image with resolving power required to determine whether the cell is normal or not, on the basis of morphological information described later.

In Step S104, a process for determining a specimen zone 42 and actually measured focal positions is executed. This process is as follows. First, on the basis of the entire image of the specimen search area 41 acquired in Step S102, a process for deciding a zone on which the specimen 19 is actually placed on the slide glass 40 (the specimen zone 42 shown in FIG. 3) is performed. The decision of the specimen zone 42 can be made by the existing method. For example, the specimen zone 42 is decided to be previously rectangular and the entire image is changed to a binary image in accordance with the presence of the specimen to search the portion where the specimen 19 is present in the X and Y directions perpendicular to each other. Also, the specimen zone 42 may be decided in such a way that the operator arbitrarily designates the specimen zone 42 by operating the mouse device and its result is acquired by the host system 2.

Subsequently, a process for dividing the decided specimen zone 42 on a hound's-tooth check pattern is performed as shown in FIG. 4. The zone size of one section (a small section) of the hound's-tooth check pattern is set in a photographing zone projected on the video camera 3 when the objective lens 23 selected in Step S103 is used. A process is executed for finding the X and Y coordinates (for example, a rectangular center coordinates, because each small section in this case is rectangular) on the image of FIG. 4 specifying the position of each small section and then for converting the X and Y coordinates on the image into physical X and Y coordinates on the motorized stage 20. Also, in a calculation method for converting the X and Y coordinates, it is desirable that a well known one is used. For example, in a method of making the calculation on the basis of the photomagnification of the entire image and the image sensor information (the number of pixels and pixel size) of the video camera 3, its details are set fort in Kokai No. Hei 9-281405.

Next, in order to decide the actually measured focal positions, a process for actually measuring focusing positions (the Z coordinates) to decide the small sections is carried out. This process may be carried out with respect to all small sections, but in this embodiment, the sections are large in number and thus, small sections to be actually measured (for example, actually measured focal position extraction points shown in FIG. 4) are extracted from among all small sections so that only the extracted, actually measured focal position extracting points are actually measured. This extraction method may be such that, for example, the small sections are extracted at random or regularly (for example, every third section). Here, for a small section in which the image of the cell of a part of the specimen 19 is not present, it is favorable that the extraction for the actual measurement of the focusing position is not considered.

In Step S105, the motorized stage 20 is moved in the X and Y directions and the position of the optical axis is moved to each of the actually measured focal point extraction points extracted in Step S104 to evaluate the contrast of the specimen image photographed by the video camera 3 while performing the Z axis movement control in accordance with the extraction point (a so-called contrast AF). Whereby, a process for finding the focusing position by actual measurement (the Z coordinates) is executed. In addition, for each of the zones (small sections) which are not extracted as the actually measured focal position extraction points in Step S104, a process for finding the focusing position (the Z coordinates), for example, by a linear interpolation calculation is performed in accordance with the actually measured focusing position (the Z coordinates) of the actually measured focal position extraction point close to this section.

The process of Step S105 is performed and thereby a focus map 50 shown as an example in FIG. 5 is produced. The focus map 50 thus produced is recorded in a photographing coordinate record section 34. For each of the small sections in which the focusing positions (the Z coordinates) are obtained, its array number 51 and stage coordinates 52 are stored in the focus map 50 shown in FIG. 5. Here, the array number 51 refers to the number specifying each small section, which is regularly allocated like 1, 2, 3, . . . in each of the X and Y directions with respect to each small section as shown in FIG. 4. For example, in a small section at the upper left-hand corner in the specimen zone 42 shown in the figure, the array number 51 is (X axis, Y axis)=(1, 1).

Also, the focus map 50 shown in FIG. 5 has the column of the Z axis in the array number 51. This becomes necessary when the three-dimensional VS image of an object of interest described later is generated. The stage coordinates 52 includes the physical X and Y coordinates on the motorized stage 20 corresponding to the center position of the small section and the Z coordinates of the motorized stage 20 indicating the focusing position by the actual measurement.

In Step S106, a process for acquiring the entire specimen VS image is performed. In this process, the motorized stage 20 is first moved in accordance with the focus map 50 produced as mentioned above to acquire the image of each section. Specifically, at the optical axis position and focusing position of the microscope apparatus 1, the motorized stage 20 is moved to the position of the X, Y, and Z coordinates stored in the focus map 50 and the microscope image of the small section (an RGB color image in which the component value of each color indicated by 8 bit data (256 gradations) in the embodiment) is photographed by the video camera 3 at the position of the X, Y, and Z coordinates and is acquired. Also, the photomagnification of the microscope image of each small section in this case is assumed as a first photomagnification.

A subsequent process is performed for mutually connecting the acquired microscope image of each small section with the microscope images of adjacent small sections to thereby construct the microscope image of the entire specimen zone 42, namely, the entire specimen VS image. The entire specimen VS image generated in this way is recorded as the image file in the data record section 4.

The processes described above are the VS image generation processing of the entire specimen. The operator, after placing the specimen 19 (the slide glass specimen) on the motorized stage 20, operates on an operation screen, not shown, and only carries out the instructions of the start of the VS image generation processing of the entire specimen. Whereby, the VS image generation processing is executed by the host system 2 to generate the entire specimen VS image constructed from the microscope image of the first photomagnification and representing the entire image of the specimen 19. Also, the image file to be recorded in the data record section 4 can be stored in a state where the data is compressed by using an image compression processing system, such as a well-known JPEG (joint photographic experts group) system or a JPEG 2000 system.

In the processes of Steps S101 and S103 in FIG. 2, the distinction between "low magnification" and "high magnification" of the objective lens 23 introduced into the optical path is such that a relative value exists, not an absolute one. For example, when a 2× or 4× magnification is assumed as a low magnification, a 10×, 20×, or 40× magnification is a high magnification, but the distinction is not limited to this example.

A slide specimen number printed in the bar code label 43 of the slide glass specimen is read out by a bar code reader, not shown, connected to the host system 2 and is recorded as the subsidiary information of the image file stored in the data record section 4. Whereby, the specimen 19 may be related to the image file. Further, shading (image blurring) caused by an illumination optical system, an imaging optical system, or an image pickup system may be eliminated in such a way that high-pass filter processing using the well-known technique, for example, an FFT (fast Fourier transform) is applied to the microscope image photographed by the video camera 3 or differential processing with the image data of only the background excluding the specimen 19 is applied thereto.

In any of Steps S101 to S106 in FIG. 2, the progress of the processing is stopped once, and the operation can be performed by the operator to enable adjustment work in individual steps, such as a change of the specimen zone 42, a change, addition, and deletion of the really measured focal position extraction point, and a magnification change of the objective lens 23 with high magnification to be used. Moreover, the optimization of the illumination system of the microscope apparatus 1 according to the changeover of the objective lens 23 may be performed.

As described in Kokai No. Hei 9-281405, the microscope system may be designed so that in the movement of the motorized stage 20 in the X and Y directions (the movement in the horizontal direction, that is, the movement on the plane perpendicular to the optical axis of the microscope apparatus 1), the regions of overlapping with the images of adjacent small sections are provided in each small section and moved to acquire the microscope image including the regions of overlapping with respect to each small section and paste processing of these images is performed. By doing so, a discontinuity attributable to the positional accuracy of the motorized stage 20 in the connected part of the entire specimen VS image can be solved. In this case, it is only necessary that the zone size of one section of the focus map 50 produced in Step S105 of FIG. 2 is set to a size that the regions of overlapping for the paste processing are eliminated from the photographing zone projected on the vides camera 3 in the use of the objective lens 23 with high magnification.

Figure 6A:
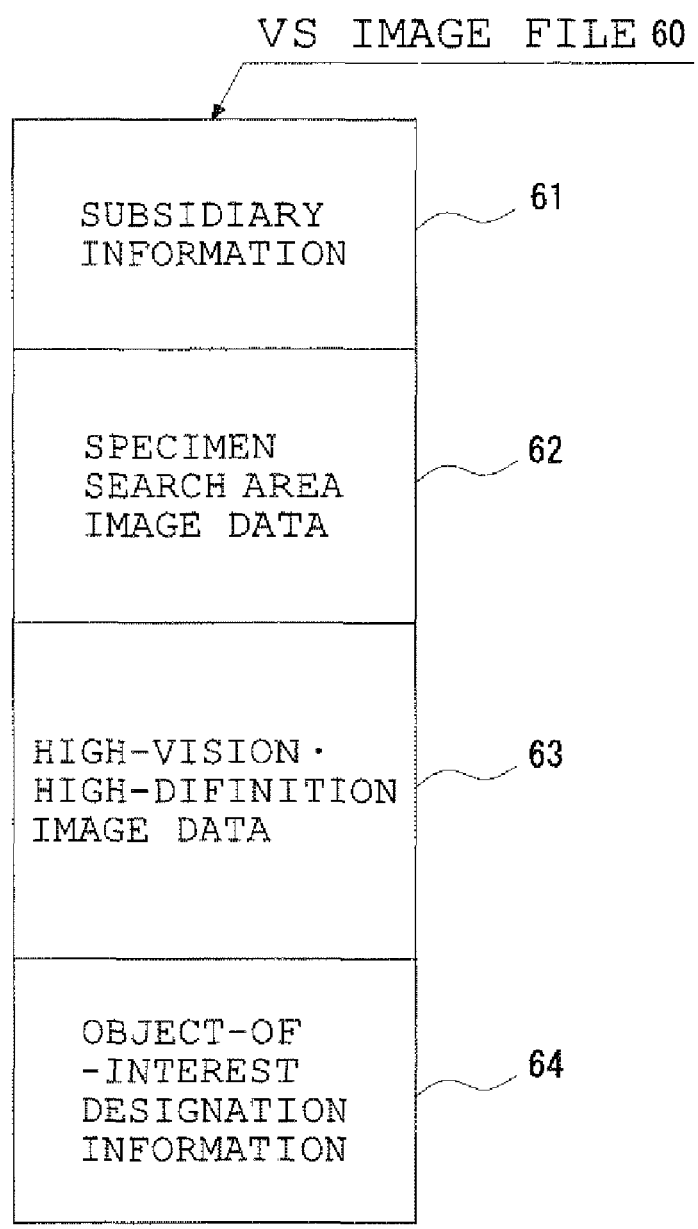
FIG. 6A is a view showing the data structure of the entire VS image file.
Figure 6B:
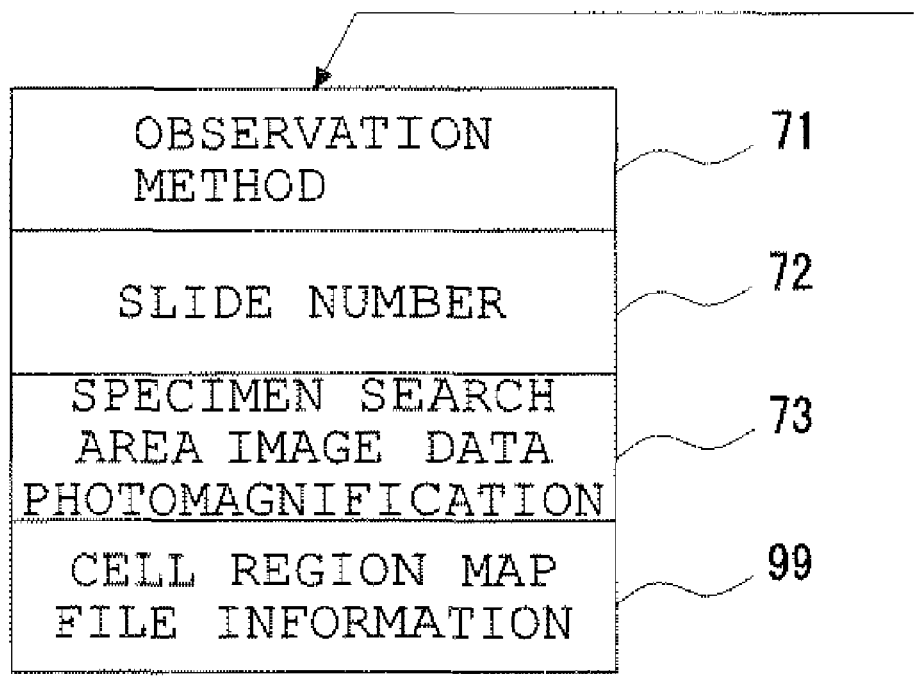
FIG. 6B is a view showing the data structure of subsidiary information.
Figure 6D:
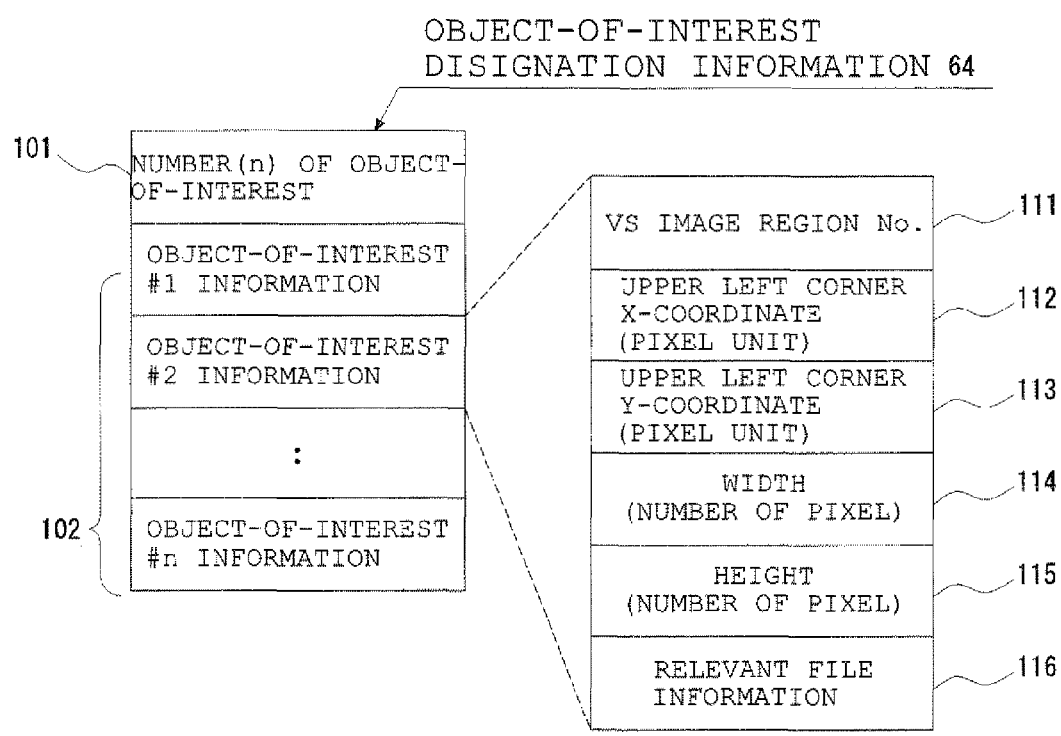
FIG. 6D is a view showing the data structure of designation information of the object of interest.

Subsequently, reference is made to FIGS. 6A to 6D. The data table shown in each of these figures gives a format example (a data structure example) of the VS image data recorded as the image file in the data record section 4. FIG. 6A shows the data structure of the entire VS image file storing the VS image data. A VS image file 60 incorporates subsidiary information 61, specimen search area image data 62, high-vision and high-definition image data 63, and object-of-interest designation information 64. FIG. 6B shows the data structure of the subsidiary information 61 stored in the VS image file. The subsidiary information 61 contains an observation technique 71, a slide number 72, a specimen research area image data photomagnification 73, and cell region map file information 99.

The observation technique 71 is the one (microscopy) adopted when the high-vision and high-definition image data 63 is acquired. In this embodiment, information on a "bright field observation technique" is stored. The slide number 72 is a discrimination number arbitrarily allocated for the slide glass specimen and, for example, information printed by bar codes in the label 43 as mentioned above is stored as the slide number 72. The specimen search area image data 62 in FIG. 6A is the image data of the entire slide image (a low-resolution image of the entire specimen search area 14) obtained by the process of Step S102 in the VS image generation processing of the entire specimen of FIG. 2 described above (that is, obtained by connecting the image captured by the objective lens 23 with low magnification). The specimen research area image data photomagnification 73 of FIG. 6B stores information indicating the magnification of the objective lens 23 (with low magnification) used when the microscope image used for the production of the specimen search area image data 62 is formed.

Also, the cell region map file information 99 in FIG. 6B will be described later. The image data 63 refers to the image data of the VS image generated by the process of Step S106 in the VS image generation processing of the entire specimen of FIG. 2 or Step S 256 in generation processing of an object-of-interest three-dimensional VS image described later and varied information according to this VS image. FIG. 6C shows the data structure of the image data 63.

By assuming the case where a plurality of VS image data are stored in the single VS image file 60, the image data 63 stores VS image region information 82 (VS image region #1 information, VS image region #2 information, and VS image region #n information) as the information of each VS image. The number of pieces of the VS image region information 82 (a value n indicating the number of #1 to #n in the example of FIG. 6C) is stored as the designation number of VS image regions 81.

Hence, when the VS image corresponds to only the entire specimen VS image generated by Step S106 in the VS image generation processing of the entire specimen of FIG. 2, the designation number of VS image regions 81 is "1", and the image data of the entire specimen VS image is stored as the VS image region #1 information in the VS image region information 82. The individual VS image region information 82 contains photographing information 83, focus map data 84, and image data 85. The photographing information 83 contains individual data, for example, of a photomagnification 91, scan starting (upper left section) stage X coordinates 92, scan starting (upper left section) stage Y coordinates 93, the number of X-direction pixels 94, the number of Y-direction pixels 95, and the number in the Z direction 96. The data of the photomagnification 91 of the photographing information 83 in the VS image region information 82 stores information indicating the magnification of the objective lens 23 in photographing the microscope image represented by the image data 85 in the VS image region information 82. The data of the scan starting (upper left section) stage X coordinates 92 and the scan starting (upper left section) stage Y coordinates 93 store the X coordinates and the Y coordinates (the coordinates on the motorized stage 20), respectively, indicating the position where the acquisition of the microscope image represented by the image data 85 is started. The data of the number of X-direction pixels 94 and the number of Y-direction pixels 95 store information indicating the size of the microscope image represented by the image data 85 in the X direction and the Y direction, respectively.

The information of the number in the Z direction 96 stores the number of sectioning zones in the Z direction in generating the object-of-interest three-dimensional VS image described later. Also, when the VS image stored in the VS image file 60 corresponds to the entire specimen VS image generated in Step S106 of FIG. 2, it is stored as the value "1" in the information of the number in the Z direction 96.

In the focus map data 84, the focus map 50 (refer to FIG. 5) produced by the processes of Step S105 in FIG. 2 and Step S256 in the generation processing of the object-of-interest three-dimensional VS image described later is stored.

The image data 85 stores the image data of the VS images generated by the processes of Step S106 in FIG. 2 and Step S256 in the generation processing of the object-of-interest three-dimensional VS image described later.

Also, information stored in the object-of-interest designation information 64 is described later because it is not produced by the process of FIG. 2.

[Setting of the Region of Interest]

A description will be given of the process that the image region in which the image of an abnormal cell, such as an atypical or malignant cell, or a cell mass is represented is set as the object of interest with respect to the entire image of the specimen 19 represented by the entire specimen VS image generated as mentioned above. Also, in the following description, a single cell or a cell mass is referred to as a "cell region" and the atypical or malignant cell as an "abnormal cell". Additionally, in the embodiment described below, the entire specimen VS image generated by the process of FIG. 2 is referred to as the "entire specimen VS color image".

Figure 7:
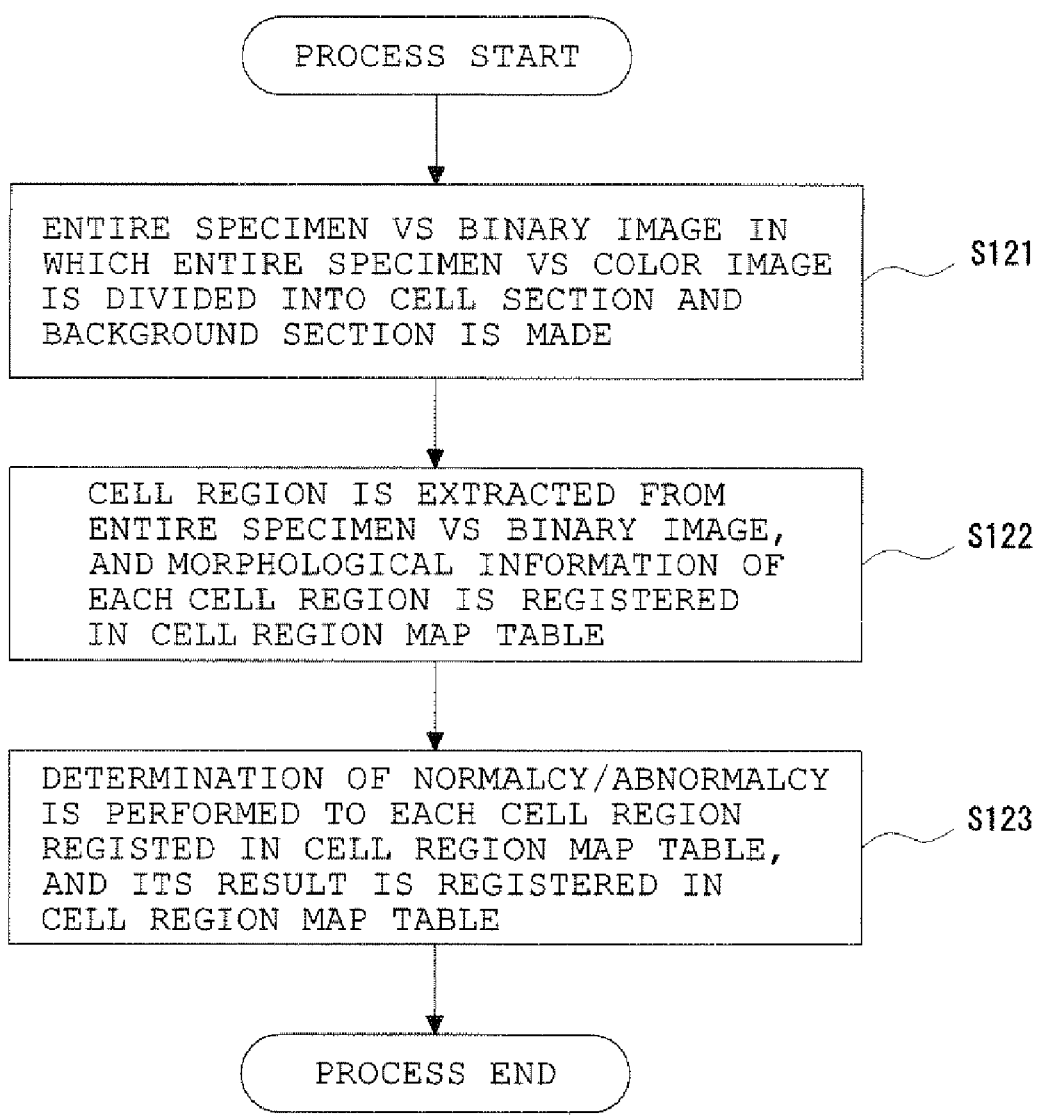
FIG. 7 is a flow chart showing the details of setting processing of the object of interest.

FIG. 7 is a flow chart showing the contents of setting processing of the object of interest, executed by the host system 2. In FIG. 7, Step S121 executes the process for generating the entire specimen VS binary image in which the entire specimen VS color image is divided into two areas, a target data section (the cell) and a non-target data section (a background section). The details of this process will be described later.

In Step S122, a process is performed for extracting a spatially connected mass (cell region) of the target data section from the VS binary image generated in Step S121 to register its morphological information in a cell region map table 130 illustrated in FIG. 8A in accordance with an extracted cell region. The details of the cell region map table 130, as well as this process, will be described later.

In Step S123, a process is performed that a determination is made as to whether the cell is normal in accordance with the cell region recorded in the cell region map table 130 and the result is registered in the cell region map table 130. Whereby, the setting of the object of interest (the cell region to be examined by the viewer) is completed. The cell region map table 130 is recorded and stored as a cell region map file in the data record section 4. In the cell region map file information 99 (refer to FIG. 6B) stored in the data record section 4, a file path to the cell region map file is previously stored. By doing so, the correspondence of the entire specimen VS color image to the cell region map table 130 is clarified and it becomes possible to follow an abnormal cell region from the entire specimen VS color image file in the processing of the recall display of the abnormal cell to be described later.

Figure 9:
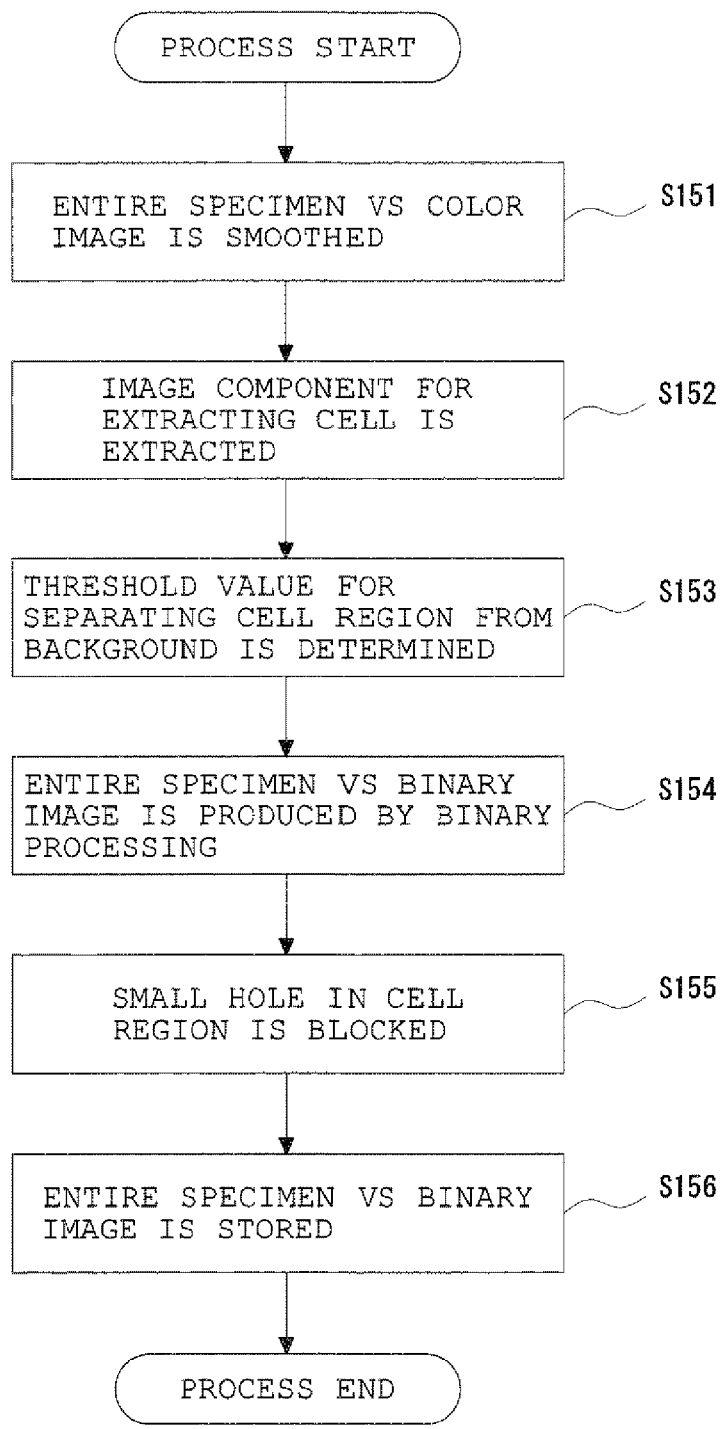
FIG. 9 is a flow chart showing the details of generation processing of a VS binary image of the entire specimen.

Next, reference is made to the contents of the processes of Steps S121, S122, and S123 in FIG. 7. The details of the process of Step S121 are described with reference with the flow chart shown in FIG. 9. In Step S151, a process is carried out that smoothing using a smoothing filter, such as a Gaussian filter, is applied to the entire specimen VS color image to lessen an unnecessary gray fluctuation. Also, this smoothing is well known as set forth, for example, in "Digital Image Processing", the supervision of Digital Image Processing Editorial Committee, Second Edition, Computer Graphic Arts Society, Mar. 1, 2007, pp. 108-110 and pp. 177-184. However, the explanation of its details is omitted here.

In Step S152, a process is performed for selecting the image component used when the image region of the cell is extracted from the entire specimen VS color image (separated from the image region of the background). As candidates of the image components usable for this extraction, various color components, for example, an R (red) color component, a G (green) color component, a B (blue) color component, a Y (luminance) component, and other components of a color system, can be nominated. However, it is desirable that the image component in which the cytoplasm can be separated from the background with accuracy is selected from among these components. Also, this appropriate image component depends on the spectral sensitivity characteristic of the video camera 3 used and hence a proper component should be selected in accordance with the characteristic of the microscope system of FIG. 1. In this embodiment, dispersion is high and the accuracy of the separation between the background and the cytoplasm is favorable. It is assume that the R (red) color component is selected from among these candidates. Hence, in Step S152, a process for producing the entire specimen VS image (R) extracting only the R (red) color component from the entire specimen VS color image is carried out.

In Step S153, a process is performed that a threshold value for separating the image region of the cell from the other (the image region of the background) is determined. The determination of this threshold value is made by the following procedure. The largest component of the entire specimen VS image (R) is background (no specimen) data. Thus, when the histogram of the R color component values is made with respect to the entirety, or a part (for example, five sections in each of the X and Y directions of the small sections shown in FIG. 4), of the VS image (R), it is obvious from the experience that a mode in this histogram becomes the largest component value as the background. It is also obvious from the experience that in the background data, the above mode takes a nearly intermediate value between the maximum and minimum of the component value. Moreover, it is further obvious from the experience that in the VS image (R), the pixel in which the component value is maximum constitutes the brightest background data.

From the above description, a value found by an expression described below is set as the threshold value for separating the image region of the cell from the other (the image region of the background).

$$\text{Mode}-(\text{Maximum value}-\text{Mode})+\text{Correction value} \quad (1)$$

Also, in Expression (1), the "correction value" is an arbitrary adjustment value in which the adjustment can be made by the system. Here, when the "correction value" is taken as "0", the value found by Expression (1) becomes the minimum of the component value of the background supposed in the VS image (R).

The determination of the threshold value for separating the image region of the cell from the other (the image region of the background) may also be made as described below. In the entire specimen VS color image, the image region of the background is generally bright (the component value is large) because individual values of the R, C, and B components constituting three primary colors of light are nearly equal (colorless) and the transmittance of illumination light is high. Hence, in the entire specimen VS color image, a region constructed with pixels in which the G component value exceeds a preset value (for example, "190"), the absolute value of the difference between the R component value and the G component value is below a preset value (for example, "2"), and the absolute value of the difference between the B component value and the G component value is below a preset value (for example, "2") is set as the image region of the background, the data of the VS image (R) corresponding to this image region is acquired as the background data, and the minimum value of the background data is determined as the threshold value.

In Step S154, a process for applying binary processing to the VS image (R) is carried out. Specifically, the threshold value found in Step S153 is used to perform binary processing that, in the VS image (R), the data below the threshold value are set to data "1" (displayed by black pixels) as the cell region and the data exceeding the threshold value are set to data "0" (displayed by white pixels) as the region other than the cell region (the background), and thereby the process for generating the entire specimen VS binary image is performed.

In Step S155, a blocking process is performed for blocking up small holes made in the image region of the cell in the entire specimen VS binary image generated. As this blocking processing, for example, closing processing for dilating and eroding the image region by the same number of times is carried out. Also, the closing processing by dilation and erosion is well known as set forth, for example, in "Digital Image Processing", the supervision of Digital Image Processing Editorial Committee, Second Edition, Computer Graphic Arts Society, Mar. 1, 2007, pp. 108-110 and pp. 177-184. However, the explanation of its details is omitted here.

In Step S156, a process is performed that the image data of the entire specimen VS binary image after the blocking processing is applied is recorded and stored as the image file in the data record section 4.

Figure 10A:
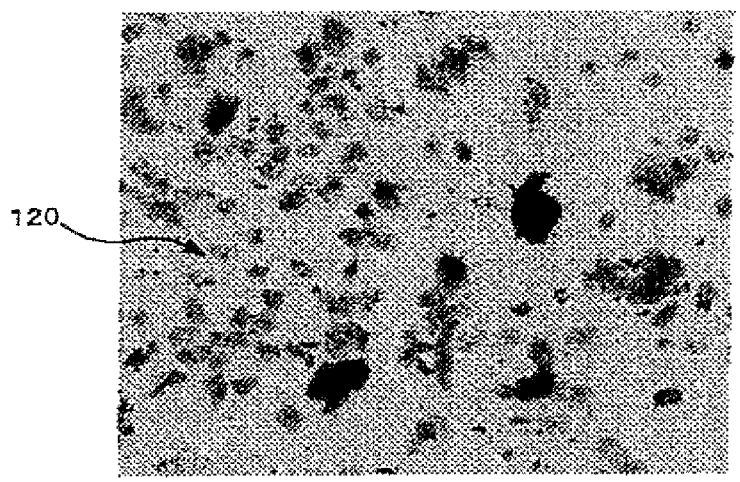
FIG. 10A is a view showing an example of the entire specimen VS image after smoothing is applied.
Figure 10B:
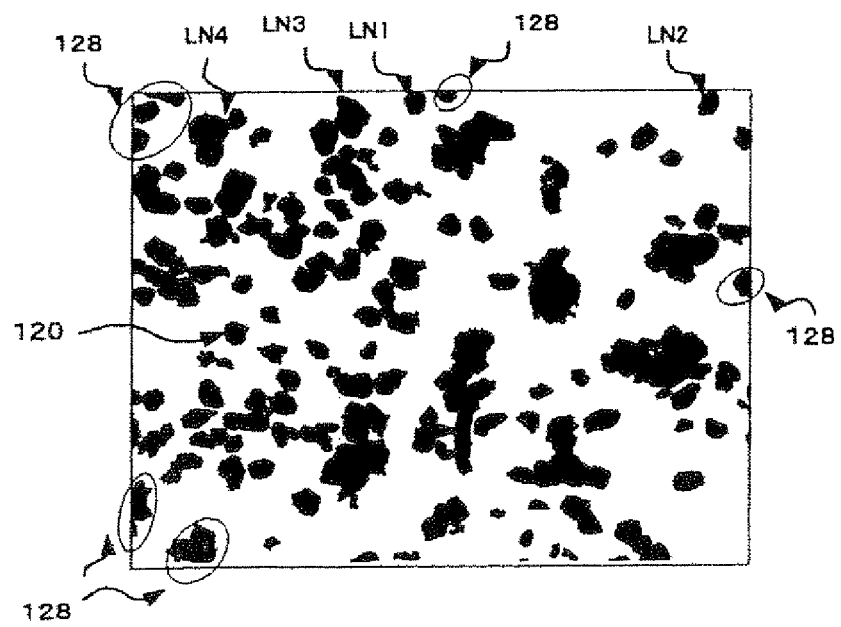
FIG. 10B is a view showing the VS binary image of the entire specimen generated from the image example of FIG. 10A.
Figure 10C:
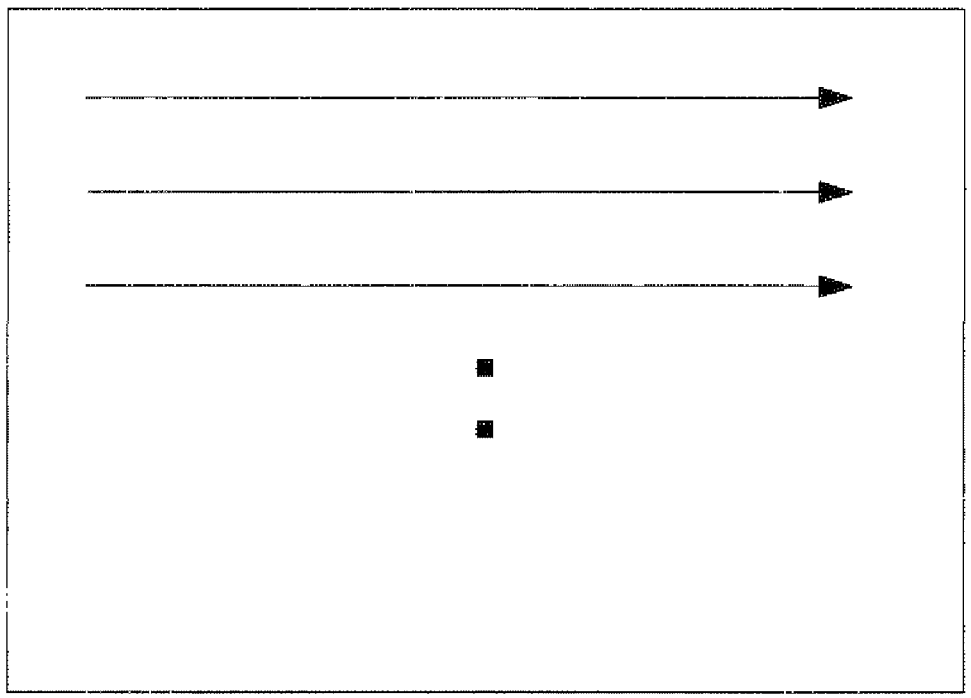
FIG. 10C is a view showing a scanning pattern in a raster scan performed with respect to the VS binary image of the entire specimen.

Next, a description will be given of the extraction process of the cell region of Step S122 in the setting processing of the object of interest shown in FIG. 7 with reference to FIGS. 10A to 10C. FIG. 10A shows an example of the VS binary image (R) after smoothing is applied by the process of Step S151 in FIG. 9. FIG. 10B shows the entire specimen VS binary image generated from the image example of FIG. 10A by the process in FIG. 9. FIG. 10C shows a scanning pattern in a raster scan performed with respect to the VS binary image in order to extract the cell region.

First, a process for extracting a cell region 120 from the VS binary image illustrated in FIG. 10B is performed. Specifically, this process can be performed in such a way as to use a well-known technique of contour tracking set forth, for example, in "Digital Image Processing", the supervision of Digital Image Processing Editorial Committee, Second Edition, Computer Graphic Arts Society, Mar. 1, 2007, pp. 108-110 and pp. 177-184, with respect to a pixel connecting component representing the cell region 120 and thereby to extract the contour of the pixel connecting component. For the cell region 120 thus extracted, labeling processing is performed using the result of the contour tracking, for instance. For this labeling processing, the process set forth, for example, in "Digital Image Processing", the supervision of Digital Image Processing Editorial Committee, Second Edition, Computer Graphic Arts Society, Mar. 1, 2007, pp. 108-110 and pp. 177-184, is cited.

In the pixel connecting component representing the cell region 120 further extracted, geometric features (geometric feature parameters), such as coordinates of a bonding box, an area, a center of gravity, a perimeter, and a roundness, are calculated and its results are registered in the cell region map table 130 (refer to FIG. 8A). For the process for calculating such geometric feature parameters, the process set forth, for example, in "Digital Image Processing", the supervision of Digital Image Processing Editorial Committee, Second Edition, Computer Graphic Arts Society, Mar. 1, 2007, pp. 108-110 and pp. 177-184, is cited.

Figure 8B:
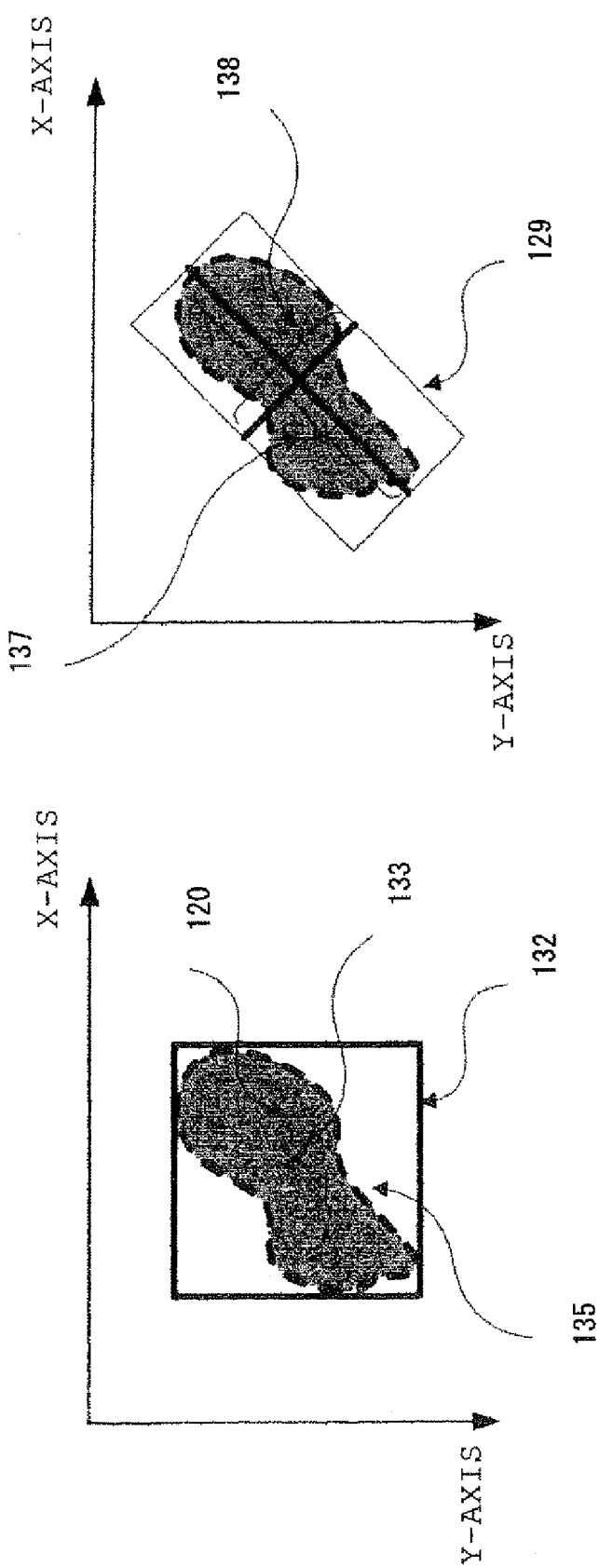
FIG. 8B is a view for explaining geometric features relative to the cell region.

In the following, an explanation on the cell region map table 130 shown in FIG. 8A is made using FIG. 8B. In a label 131 (FIG. 8A), labels (numbers) provided for the extracted cell regions 120 are given in consecutive numbers.

As shown in FIG. 8B, the X and Y coordinates, on the VS binary image, of a bounding box 132 which is circumscribed about the cell region 120 and in which each side is parallel with the X or Y axis and a width (W) in the X direction and a height (H) in the Y direction are found with the unit of a pixel value and stored. In a center of gravity 133, the position of the center of gravity of the cell region 120 is stored as the X and Y coordinates on the VS binary image. In an area 134 (FIG. 8A), the area of the cell region 120 is stored. Also, since the actual dimension of one pixel of the VS binary image is found on the basis of the size of one pixel (assumed as a square pixel) and photomagnification of the video camera 3, the conversion from the number of pixels into the actual dimension is easily carried out.

In a perimeter 135 (the length of a broken line shown in FIG. 8B), the length of the outer contour of the cell region 120 is stored. In a roundness 136, the value of an expression, "4π×area÷perimeter", is stored. Also, the value of this expression reaches the maximum value 1 when the contour geometry of the cell region 120 is a real circle, and diminishes as the contour geometry becomes complicated. In a major diameter 137 and a minor diameter 138, the lengths of a major side and a minor side, respectively, where a rectangle 129 circumscribed about the cell region 120 has a minimum area are stored. In an aspect ratio 139, the value of an expression, "major diameter÷minor diameter", is stored.

Values in columns other than those described relative to the map table 130 shown in FIG. 8A, which are not stored by the extraction processing of the cell region in Step S122, will be described later. For example, when the raster scan in the scanning pattern illustrated in FIG. 10C is performed with respect to the entire region of the entire specimen VS binary image to carry out the process for extracting the cell region mentioned above, the cell regions are stored in order of LN1, LN2, LN3, . . . , as shown in FIG. 10B.

Also, in order to avoid extracting neutrophiles and fine necrotic substances when the cell region 120 is extracted, the major diameter and/or the area or a target below the preset value may be excluded without being recognized as the cell region. A cell region coming in contact with the side of the VS binary image (for example, a cell region 128 in FIG. 10B) may be excluded without being recognized as the cell region because its original contour is unclear.

Subsequently, a description will be given of the details of determination processing for normality/abnormality of the cell region 120 which is the process of Step S123 in the setting processing of the object of interest shown in FIG. 7 with reference to the flow chart in FIG. 11. In Step S181, for example, a process is carried out that smoothing using a smoothing filter, such as a Gaussian filter, is applied to the entire specimen VS color image to lessen an unnecessary gray fluctuation. The image after the smoothing is applied by this process is hereinafter referred to as a "smoothed entire specimen VS color image". Instead of this process, the image data of the smoothed entire specimen VS color image obtained by the process of Step S151 in FIG. 9 may be stored as the image file in the data record section 4 so that the image data is read Out.

In Step S182, a process is performed that a label variable LN which is a variable used to separately select the cell regions 120 registered in the cell region map table 130 is initialized to "1". In Step S183, a process is performed that cell region information corresponding to the present value of the label variable LN is acquired from the cell region map table 130 to refer to the cell region 120 corresponding to the cell region information in the smoothed entire specimen VS color image and the cell region 120 is divided into two areas, a nucleus region and the other (the cytoplasm). The details of this process will be described later. In Step S184, a process is performed that a determination is made as to whether the cell region 120 in reference is a single cell of solitary scattering (which is hereinafter referred to as a "solitary scattered cell") or a cell mass which is a mass including a plurality of cells. In the embodiment, this determination processing is carried out as follows.

First, when the cell region 120 satisfies all Conditions 1-3 described below, the determination that the cell region 120 is the solitary scattered cell is made, and when the cell region 120 fails to satisfy at least one of Conditions 1-3, the determination that the cell region 120 is the cell mass is made:

Condition 1: the area of the cell region 120 is below a preset value (for example, 3000 $\mu m^2$).
Condition 2: the major diameter of the cell region 120 is below a preset value (for example, 60 $\mu m$)
Condition 3: at most one nucleus exists within the cell region 120.

In the determination processing of Step-S184, when the determination that the cell region 120 is the solitary scattered cell is made (namely, when the result of the determination is Yes), the determination processing for normality/abnormality is performed relative to the solitary scattered cell in Step S185 and then the process is advanced to Step S187. On the other hand, in the determination processing of Step S184, the determination that the cell region 120 is the cell mass is made (when the result of the determination is No), the determination processing for normality/abnormality is performed relative to the cell mass in Step S186 and then the process is advanced to Step S187. Also, although the details of the determination processing for normality/abnormality relative to each of the solitary scattered cell and the cell mass are described later, the result of the determination obtained by this processing is registered in the cell region information concerning the cell region 120 in reference in the cell region map table 130.

In Step S187, a process for renewing the label variable LN to increase its value by "1" is performed. After that, in Step S188, a process is performed that a determination is made as to whether the determination processing for normality/abnormality has been completed with respect to all the cell regions 120 registered in the cell region map table 130. Here, when it is determined that the determination processing has been completed with respect to all the cell regions 120 (namely, when the result of the determination is Yes), the process of FIG. 11 is completed. On the other hand, when it is determined that the cell regions 120 in which the determination processing is not yet performed are made to remain (when the result of the determination is No), the processing is returned to Step S183 so that the above procedures are carried out again.

Figure 12A:
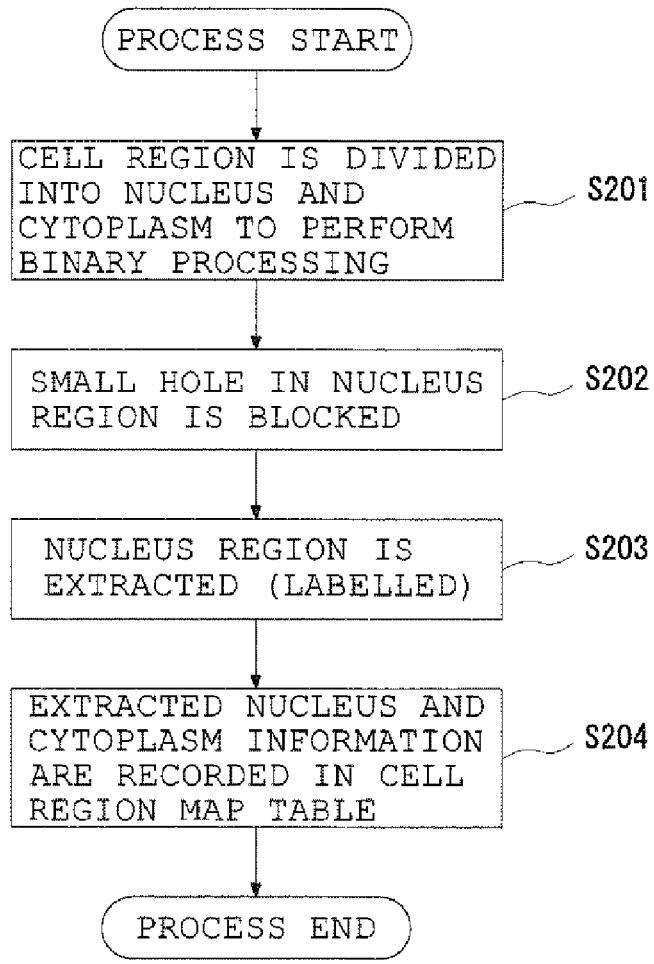
FIG. 12A is a flow chart showing the details of processing in which the cell region is separated into a nucleus region and a cytoplasm region.
Figure 12B:
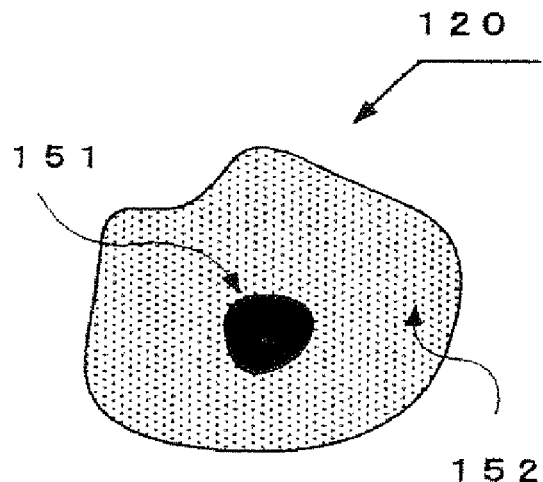
FIG. 12B is a view showing schematically the nucleus and cytoplasm in the cell region.
Figure 12C:
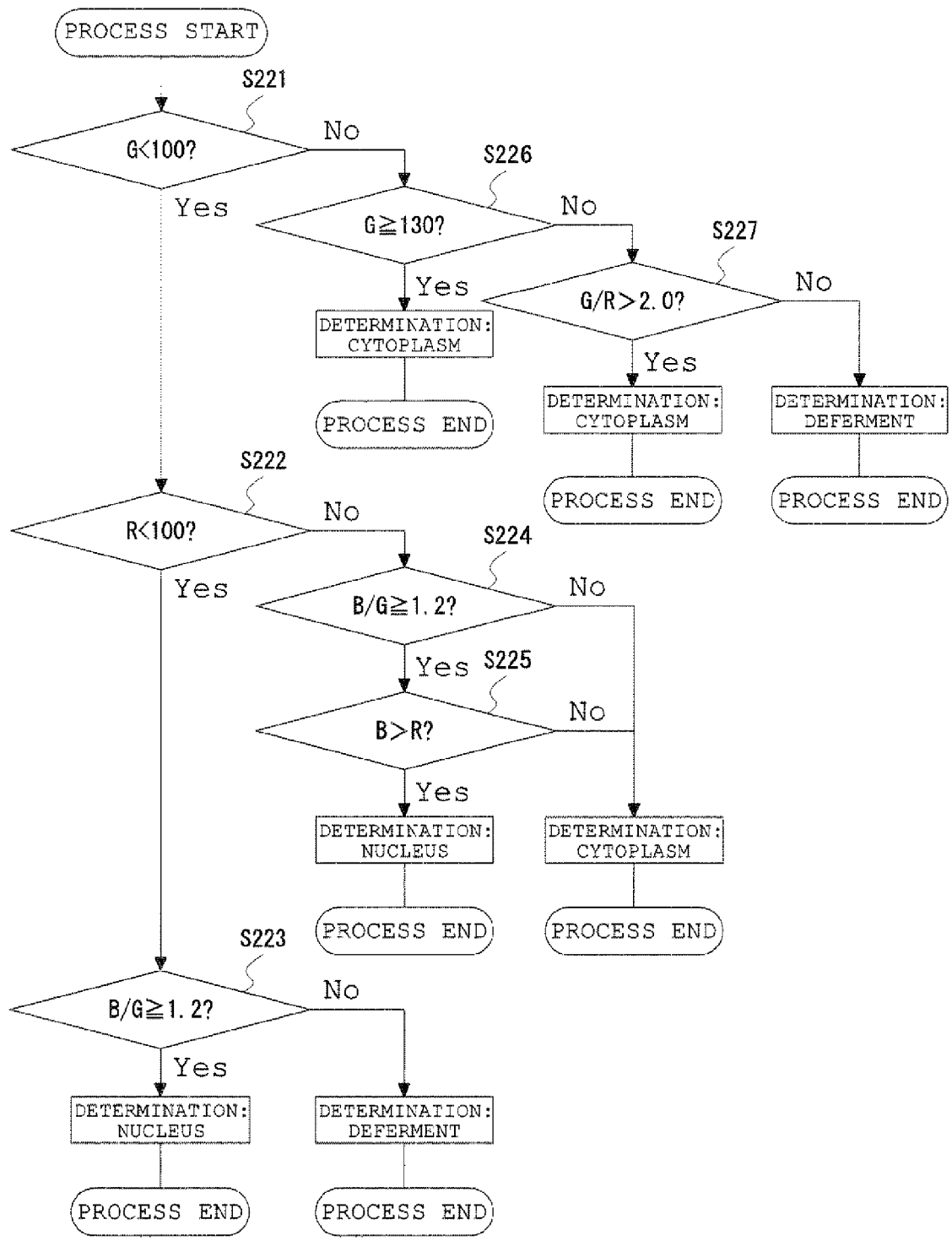
FIG. 12C is a flow chart showing distinction algorithm relative to the nucleus and the cytoplasm.

Subsequently, with reference to FIGS. 12A-12D, a description will be given of the process for dividing the cell region 120 into the nucleus region and the cytoplasm region which is the process of Step S183. FIG. 12A is a flow chart showing the details of processing in which the cell region 120 is separated into the nucleus region and the cytoplasm region. FIG. 12B is a view showing schematically the nucleus and cytoplasm in the cell region 120. FIG. 12C is a flow chart showing distinction algorithm relative to the nucleus and the cytoplasm. FIG. 12D is a view showing an example of a nucleus region map table.

In Step S201 of FIG. 12A, binary processing is performed that pixels constituting the image of the cell region 120 in the smoothed entire specimen VS color image, as shown in FIG. 12B, are divided into two pixel groups, one pixel group constituting the image of a nucleus 151 and the other pixel group constituting the image of a cytoplasm. In the embodiment, this processing is carried out as follows.

The pixels constituting the image of the nucleus 151 generally have the following features:
Feature 1: the R component and the G component are both low (for example, R<100 and G<100).
Feature 2: the B component is larger than the G component (for example, B/G$\geq$1.2).
Feature 3: the R component is equivalent to or larger than the G component (namely, R$\geq$G).

The pixels constituting the image of the cytoplasm 152 generally have the following features:
Feature 4: the B component is nearly equal to the G component (for example, B/G<1.2)
Feature 5: when there is no overlapping of the cells, the G component is higher than the G component of the nucleus 151.

The pixels constituting the image of an overlapping portion of the cells in the cytoplasm 152 generally have the following features:
Feature 6: the cytoplasm 152 in which the cells overlap is darker than the cytoplasm 152 in which the cells do not overlap (for example, G<130).
Feature 7: the R component is significantly smaller than the G component (for example, G/R>2.0).

The flow chart showing an algorithm example according to the embodiment in which the tendencies of Features 1-7 mentioned above are utilized to determine the pixels constituting the image of the nucleus 151 and the pixels constituting the image of the cytoplasm 152 from the pixels constituting the image of the cell region 120, is given in FIG. 12C. In FIG. 12C, the determination processing of Steps S221 and S222 utilizes Feature 1 and the determination processing of Step S223 utilizes Feature 2. Further, the determination processing of Step S224 utilizes Feature 4, and the determination processing of Step S225 utilizes Feature 3 in consideration of the determination processing of Steps S221, S222, and S 224. In addition, the determination processing of Step S226 utilizes Features 5 and 6 and the determination processing of Step S227 utilizes Feature 7.

In the embodiment, as mentioned above, the pixels constituting the image of the cell region 120 are divided into the pixels constituting the image of the nucleus 151 and the pixels constituting the image of the cytoplasm 152 on the basis of the three primary colors (the R, G, and B components) of light in the pixels constituting the image of the cell region 120 in the smoothed entire specimen VS color image. Also, in this division processing, for pixels in which a determination cannot be made as to whether they are the pixels constituting the image of the nucleus 151 or the cytoplasm 152 and is deferred, when it has been determined that all of four pixels located vertically and laterally, of the deferred pixels constitute the image of the nucleus 151 after the determination of the pixels constituting the image of the cell region 120 has been completed, it is determined that the deferred pixels constitute the image of the nucleus 151 and others constitute the image of the cytoplasm 152.

Instead of dividing the cell region 120 into the pixels constituting the image of the nucleus 151 and the pixels constituting the image of the cytoplasm 152 as mentioned above, it is also possible to separate the nucleus 151 and the cytoplasm 152, for example, with the H component in the HSI color system representing the color with three components of hue, saturation, and intensity. Since the H component of the nucleus is, for example, within 205-300 degrees and the cytoplasm can be separated as another H component, the cell region can also be separated into the pixels constituting the image of the nucleus 151 and the pixels constituting the image of the cytoplasm 152 by using the H component. Moreover, the discrimination by the distinction algorithm shown in FIG. 12C may be performed parallel with that by the H component of the HIS color system so that only the pixels constituting the image of the nucleus 151 determined by both are finally determined as the pixels constituting the image of the nucleus 151.

As mentioned above, by the RBG components of the pixels constituting the image of the cell region 120 in the smoothed entire specimen VS color image and the component ratio between the pixels or various color spatial components in the HIS color system or the Lab color system and a combination of the components, the pixels can be distinguished into the pixels constituting the image of the nucleus 151 and the pixels constituting the image of the cytoplasm 152. Also, in Step S201, the process is also performed that the binary processing for giving the data "1" (displayed by black pixels) to the pixels constituting the nucleus 151 and the data "0" (displayed by white pixels) to the pixels constituting the cytoplasm 152 is carried out to produce the binary image of the nucleus cell region.

In Step S202, a blocking process is performed for blocking up small holes made in the nucleus 151 with respect to the produced binary image of the nucleus cell region. Also, this process may be identical with the process, for example, of Step S155 in the production processing of the entire specimen VS binary image mentioned above.

In Step S203, like the process of Step S122 in the setting processing of the object of interest shown in FIG. 7, a process is performed for extracting the region of the nucleus 151 from the binary image of the nucleus cell region to label the region and for calculating the geometric features (the geometric feature parameters) relative to the pixel connecting component representing the region of the further extracted nucleus 151 to register the calculation result in the map table 160 (FIG. 12D) of the nucleus region.

Although the detailed explanation of the map table 160 of the nucleus region shown in FIG. 12D is omitted, information stored in individual columns of the label, bonding box, center of gravity, area, perimeter, roundness, major diameter, minor diameter, and aspect ratio in the map table 160 is the same as in the cell region map table 130 shown in FIG. 8A with the exception that its targets are the region of the nucleus 151 and the cell region 120. Also, an estimated number of nuclei 151 existing in the cell region 120 can be predicted in accordance with the area of the cell region 120. Specifically, for example, when it is assumed that the average area of the cell is 5000 μm$^2$ and one nucleus exists therein, the estimated number of the nuclei 151 existing in the cell region 120 can be predicted. In the process of Step S203, therefore, when the relation ship between the number and the areas of the nuclei 151 in the extracted region deviates extremely from this predicted result, it is only necessary that various threshold values using for the distinction between the nucleus 151 and the cytoplasm 152 illustrated in FIG. 12C are changed so that a reseparation process is performed.

In Step S204, a process is performed for registering information on the nucleus 151 and the cytoplasm 152, as information on the cell region 120 containing these, in the cell region map table 130 (FIG. 8A), and a series of processes shown in FIG. 12A is completed.

In the following, reference is made to the information of the nucleus 151 and the cytoplasm 152 stored in the cell region map table 130 in accordance with FIG. 8A. In FIG. 8A, the number of the nuclei 151 existing in the cell region 120 is stored in the column of the number of nuclei 141. The average value of areas of the nuclei 151 existing in the cell region 120 is stored in the column of a nucleus area 142, and the dispersion value of areas of the nuclei 151 existing in the cell region 120 is store in the column of a nucleus dispersion 143. The average luminance value of the nuclei 151 existing in the cell region 120 in the entire specimen VS color image is stored in the column of a nucleus luminance 144. Also, in accordance with the R, B, and G component values of the pixels, a luminance Y of the pixels constituting the image of the nucleus 151 in the entire specimen VS color image can be calculated from the following expression:

$$Y = 0.29891R + 0.58661G + 0.11448B \qquad (2)$$

In the column of a cytoplasm luminance 146, the average luminance value of the cytoplasm 152 in the cell region 120 in the entire specimen VS color image is calculated and stored as in the nucleus luminance 144. In the column of an N/C ratio 145, a value calculated by the expression, "total area of the nucleus 151/total area of the cytoplasm 152", with respect to the cell region 120 is stored. Also, the columns of a determination 147, an image ID 148, and a confirmed flag 149 will be explained later.

Next, in accordance with FIGS. 13A-13D, a description will be given of the determination processing for normality/abnormality relative to the solitary scattered cell and the cell mass which is the processes of Steps S185 and S186. FIG. 13A shows a table in which items used for the abnormality determination of the solitary scattered cell and its levels (degrees of abnormality) are listed. FIG. 13B shows a determination table used for the abnormality determination of the solitary scattered cell.

In the table of FIG. 13A, the column indicates the item and the row indicates the level. Here, in the level, it is assumed that the abnormality increases in order of I→IIa→IIb→III. Also, in the columns of the table, qualitative contents, such as "dark" and "bright", are described, but actually, the level is determined on the basis of a numerical quantitative determination condition.

In the process of Step S185 in the determination processing for normality/abnormality of the cell region, a level determination is made according to the table of FIG. 13A, on the basis of an N/C ratio (namely, an area ratio between the nucleus and the cytoplasm), a nucleus area, a nucleus luminance, and a cytoplasm luminance in the solitary scattered cell. In this processing, the determination for normality/abnormality relative to the solitary scattered cell is made on the basis of at least one of the geometric feature parameter relative to the image of the cell represented by the entire specimen VS image and the image feature parameter (such as a luminance value) relative to the image of the cell. In this embodiment, the determination for normality/abnormality relative to the solitary scattered cell is made on the basis of the areas of images of the nucleus 151 and the cytoplasm 152 constituting the cell represented in the cell region 120 of the entire specimen VS color image and the luminance of images of the nucleus 151 and the cytoplasm 152 in the cell region 120. In the determination table of FIG. 13B, one which corresponds to a combination of results of this determination is the result of the determination for normality/abnormality relative to the solitary scattered cell. The result of the determination is stored in the column of the determination 147 of the cell region map table 130 (FIG. 8A). Specifically, information indicating "normal" or "abnormal" which is the result of the determination is stored in a determination classification 147a of the cell region map table 130. In a determination score 147b, a score numerical value indicating each of abnormal levels ranging from "0" to "10" is recorded. Here, the level "0" indicates that the cell is normal and the levels "1" to "10" indicate the degrees of abnormality divided into 10 ranks. Also, the level "10" indicates that the degree of abnormality is maximum.

The determination processing for abnormality of the cell mass which is the process of Step S186 is the same as the process of Step S185, with the exception that the table used for the determination, instead of the tables shown in FIGS. 13A and 13B, employs a table shown in FIG. 13C in which items used for the abnormality determination of the cell mass and its abnormality levels (degrees of abnormality) are listed and a determination table shown in FIG. 13D used for the abnormality determination of the cell mass.

In the embodiment, the determination for normality/abnormality relative to each of the solitary scattered cell and the cell mass and the determination of its degree of abnormality are made on the basis of the areas of the nucleus 151 and the cytoplasm 152 constituting the cell represented in the cell region 120 of the entire specimen VS color image and the luminance of images of the nucleus 151 and the cytoplasm 152 in the cell region 120. Also, it is also possible that such a determination is made on the basis of another geometric feature parameter, such as the aspect ratio 139, registered in the cell region map table 130 of FIG. 8A.

The setting processing of the object of interest described above is performed by the host system 2 and thereby the object of interest (the region representing the image of an abnormal cell, of the cells constituting the specimen 19) is set with respect to the entire image of the specimen 19 represented by the entire specimen VS color image so that the location of the abnormal cell in the specimen 19 is specified.

[Generation of Object-of-Interest Three-Dimensional VS Image]

Figure 14:
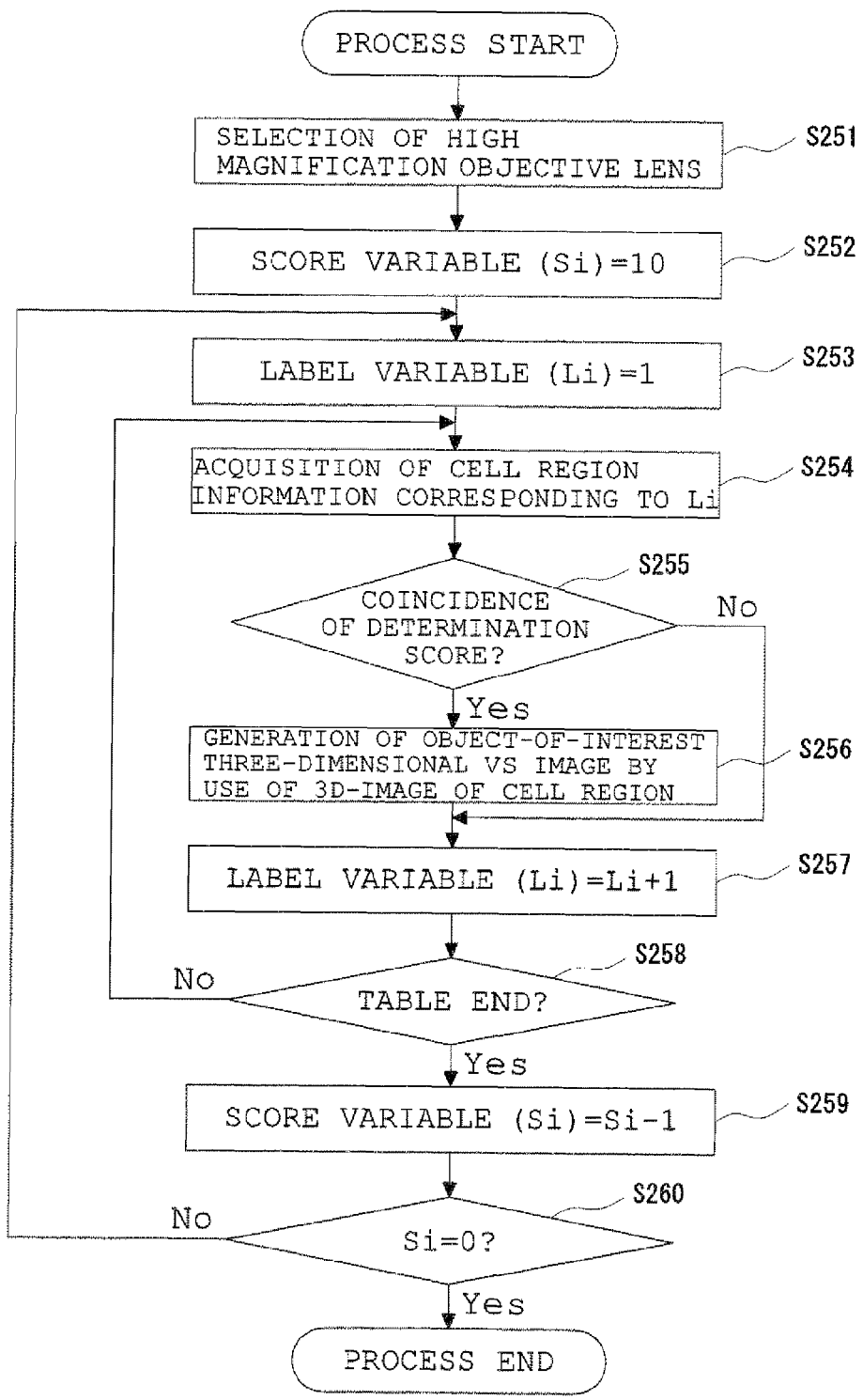
FIG. 14 is a flow chart showing the details of generation processing of the object-of-interest three-dimensional VS image.

Subsequently, in accordance with FIG. 14, a reference is made to the technique in which the abnormal cell extracted from the setting processing of the object of interest is sectioning-photographed with higher photomagnification and by changing the focal position to produce the three-dimensional VS image of the abnormal cell (the object-of-interest three-dimensional VS image). FIG. 14 is a flow chart showing the details of generation processing of the object-of-interest three-dimensional VS image.

In FIG. 14, Step S251 performs a process in which the revolver 24 is controlled and the objective lens 23 with higher (for example, 40×) magnification than that used when the entire specimen VS color image is generated (in Step S103 of FIG. 2) is introduced into the optical path. It is desirable that the magnification of the objective lens 23 introduced into the optical path at this time is one of the extent that a nucleus finding of the cell can be observed.

In Step S252, a process is performed that the maximum value ("10" in the embodiment) stored in the column of the determination score 147a of the cell region map table 130 (FIG. 8) is set as an initial value with respect to a score variable Si. This processing is started from the cell region 120 of high abnormality. In Step S253, a process is carried out that a label variable Li used to separately select the cell regions 120 registered in the cell region map table 130 is initialized to "1".

In Step S254, a process is performed for acquiring cell region information corresponding to the existing value of the label variable Li from the cell region map table 130. In Step S255, a process is performed that a determination is made as to whether the value of the determination score 147b in the acquired cell region information coincides with the existing value of the score variable Si. Here, when it is determined that both coincide (namely, when the result of the determination is Yes), a process is carried out that in Step S256, the object of interest specified by the information of the bounding box 132 in the acquired cell region information is sectioning-photographed by changing the focal position to generate the object-of-interest three-dimensional VS image. After that, the process is advanced to Step S257. On the other hand, when it is determined that both do not coincide (namely, when the result of the determination is No), the process is advanced to Step S257 without generating the object-of-interest three-dimensional VS image.

The technique of sectioning-photographing the object of interest by changing the focal position to generate the object-of-interest three-dimensional VS image is well known, for example, as set forth in Kokai No. Hei 9-281405 or 2006-343573, and thus this technique is briefly explained below.

First, the photographing area (the X and Y coordinates) is specified by the photographing information 83 (the photo-magnification 91, the scan starting stage X coordinates 92, the scan starting stage Y coordinates 93, the number of X-direction pixels 94, and the number of Y-direction pixels 95) recorded in the VS image file 60 of the entire specimen VS color image and the bounding box 132 registered in the cell region map table 130.

For the X and Y coordinates finding the focal position, coordinates designated by the center of gravity 133 registered in the cell region map table 130 or coordinates located proximate to the center of the bounding box 132 in which the cell exists are selected. The general location of the focal position (the Z axis) is acquired from the focus map data 84 (namely, the focus map 50 of FIG. 5) recorded in the VS image file 60 of the entire specimen VS color image and is set. The stage Z drive control section 22 is controlled to drive the motorized stage 20 in the Z direction and at the same time, the focusing evaluation of the microscope image captured by the video camera 3 is done. Whereby, a fine adjustment is made and an actual focus center position is decided. After that, the sectioning in the direction of the Z axis is performed, with the focus center position as a center. Also, a distance space (a sectioning step) in the direction of the Z axis and the number of photographs of microscope images are decided in accordance with the depth of field of the objective lens 23 selected in Step S251.

The photographing area set as mentioned above is photographed according to the fixed sectioning step and number of photographs. The photomagnification of the microscope obtained in this case is assumed as the second photomagnification higher than the first photomagnification described above. The microscope images at different focal positions are mutually connected according to the same focal position to generate the three-dimensional VS image of the abnormal cell (the object-of-interest three-dimensional VS image). The object-of-interest three-dimensional VS image thus generated is preserved as the image file in the data record section 4. Information on the region of interest represented by the object-of-interest three-dimensional VS image is registered in the objects-of-interest designation information 64 (FIG. 6D) in the VS image file of the entire specimen VS color image.

Also, in a VS image region No. 111 in the object-of-interest designation information 64, the details of the label 131 specifying the cell region 120 which is the object of interest represented by the object-of-interest three-dimensional VS image are registered. On the other hand, in the image ID 148 of the cell region map table 130 (FIG. 8A), one of the consecutive numbers (1 to n) for distinguishing the correspondence of the information of the object of interest in the object-of-interest designation information 64 of the VS image file 60 to the cell region map table 130 is recorded. Whereby, the correspondence of the VS image file 60 of the entire specimen VS color image to the cell region map table 130, or vice versa, is facilitated.

By the above process in Step S256, the object-of-interest three-dimensional VS image is generated which is constructed from the microscope image of the second photomagnification higher than the first photomagnification and represents the image of the object of interest in the specimen 19.

In Step S257, a process is performed for renewing the label variable Li to increase the value by "1". Next, in Step S258, a determination is made as to whether the reference of the cell region map table 130 by the label variable Li reaches the table end to complete the determination of the coincidence or discordance between the value of the determination score 147b and the existing value of the score variable Si with respect to all the cell region information registered in the cell region map table 130. Here, when it is determined that the determination of the coincidence or discordance is completed with respect to all the cell region information (namely, when the result of the determination is Yes), the process is advanced to Step S259. On the other hand, when it is determined that the cell region information in which the determination of the coincidence or discordance is not yet made is made to remain (namely, when the result of the determination is No), the process is returned to Step S254 so that the above procedures are repeated.

In Step S 259, a process is performed for renewing the score variable Si to decrease the value by "1". After that, in Step S260, a determination is made as to whether the existing value of the score variable Si becomes "0" to complete the determination of the coincidence or discordance between the values of all the determination scores 147b indicating that the cell region 120 is abnormal and the score variable Si. Here, when it is determined that the determination of the coincidence or discordance is completed with respect to the values of all the determination scores 147a (namely, when the result of the determination is Yes), the process of FIG. 14 is ended. On the other hand, when it is determined that the existing value of the score variable Si is not "0" and the value of the determination score 147b in which the determination of the coincidence or discordance is not yet made is made to remain (namely, when the result of the determination is No), the process is returned to Step S253 so that the above procedures are repeated.

The generation processing of the object-of-interest three-dimensional VS image described above is performed by the host system 2 to thereby generate the object-of-interest three-dimensional VS image constructed from the microscope image of the second photomagnification higher than the first photomagnification and representing the image of the object of interest in the specimen 19. This object-of-interest three-dimensional VS image is generated in order of increasing value of the determination score 147a relative to the abnormal cell as the object of interest, namely, in order of heightening degree of abnormality. Also, when photographic processing is performed with respect to all the abnormality levels indicated by the determination scores 147b, a vast number of photographs in the cell region 120 may be required. In this case, it is also possible that when photography reaches a preset number of photographs, the photographic processing is completed at this point of time so that the object-of-interest three-dimensional VS image is generated from the microscope image obtained so far.

[Recall Display of Object-of-Interest Three-Dimensional VS Image]

Subsequently, the recall display of the object-of-interest three-dimensional VS image will be described. This is that the object-of-interest three-dimensional VD images in the objects of interest are displayed in preset order. Also, here, the object-of-interest three-dimensional VS images of abnormal cells are displayed in order of degree, beginning with the highest, of the abnormality.

Figure 15A:
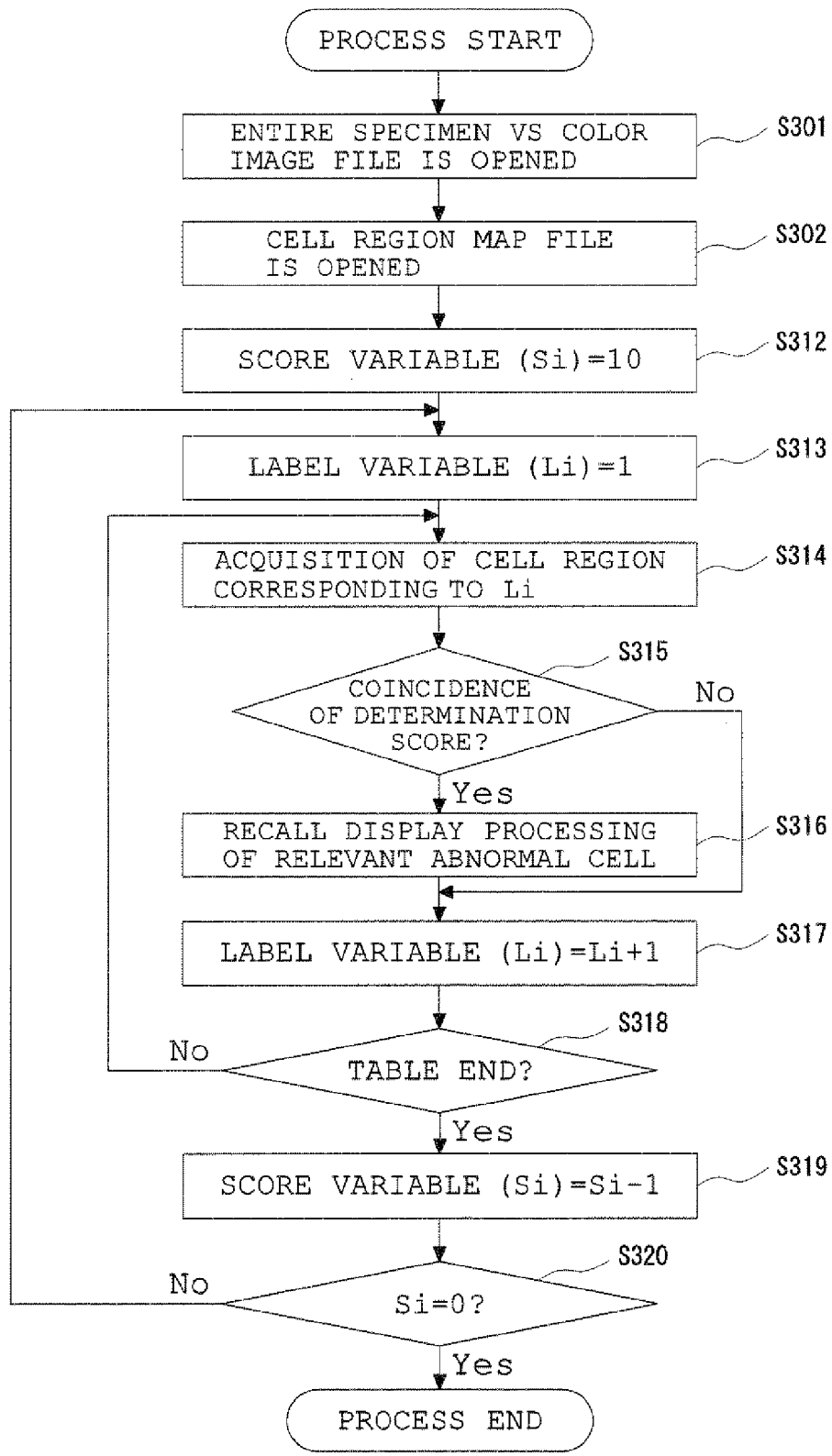
FIG. 15A is a flow chart showing the details of the processing of the recall display of the object-of-interest three-dimensional VS image.

In FIG. 15A, the details of the processing of the recall display of the object-of-interest three-dimensional VS image are shown on the flow chart. Since the flow chart shown in FIG. 15A is similar to that of the generation processing of the object-of-interest three-dimensional VS image in FIG. 14, differences between both are mainly described here.

First, in Step S301, a process is performed for opening the VS image file 60 (FIG. 6A) of the entire specimen VS color image stored in the data record section 4. In Step S302, the cell region map file stored in the cell region map file information 99 within the opened VS image file 60 is opened to bring F the cell region map table 130 (FIG. 8A) to a referenceable state. When succeeding processes from Step S312 to Step S320 are compared with those from Step S252 to Step S320 in FIG. 14, the details of both processes are the same with the exception of the processes of Step S316 and Step S256. Such as, in the following, reference is made to only the recall display of the abnormal cell which is the process of Step S316.

Figure 15B:
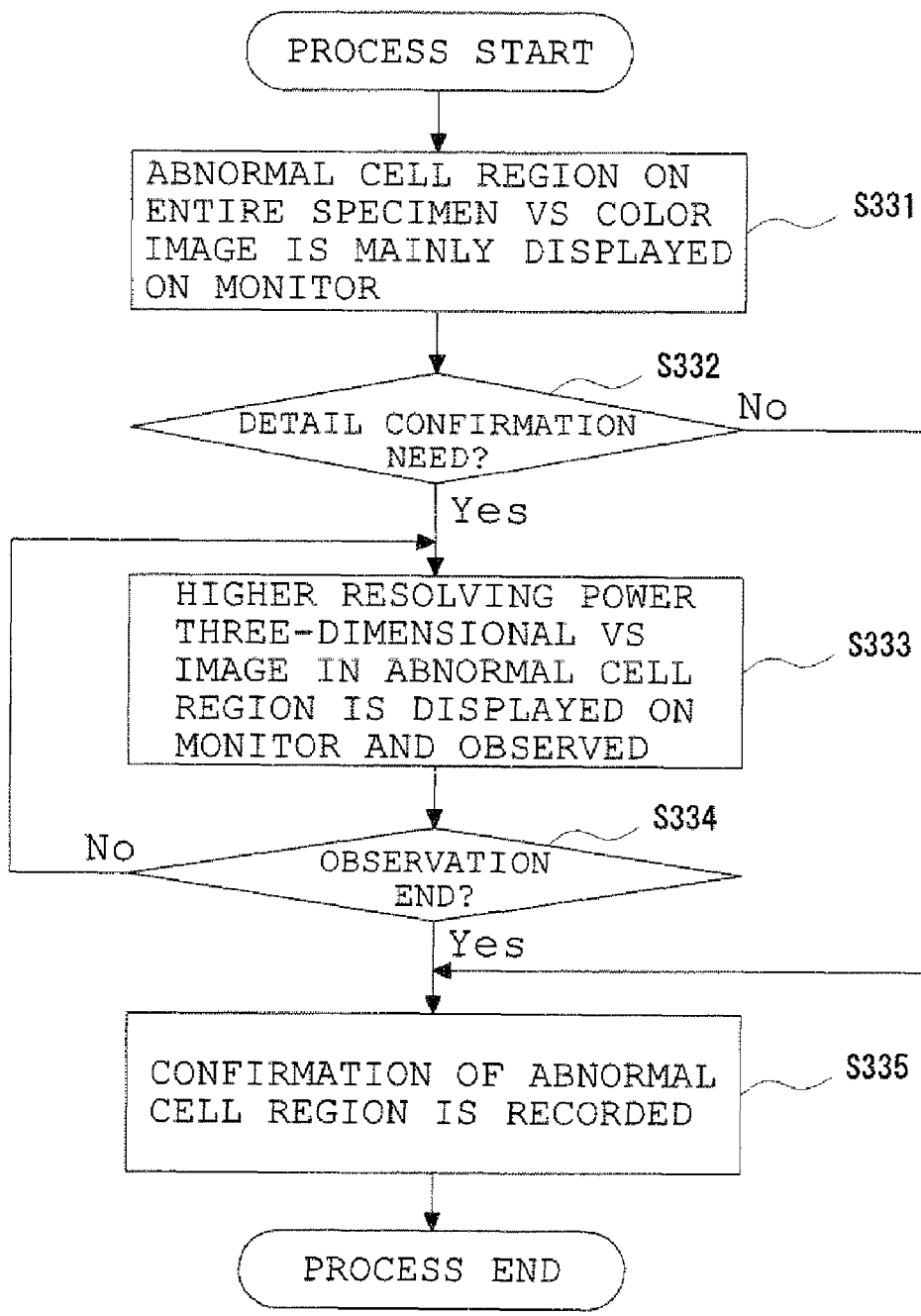
FIG. 15B is a flow chart showing the details of the processing of the recall display of the abnormal cell.

FIG. 15B is a flow chart showing the details of the processing of the recall display of the abnormal cell which is the process of Step S316 in FIG. 15A. First, in Step S331, a process is performed for displaying the entire specimen VS color image on the monitor 5. However, this display process is carried out so that the image of the cell region 120 (that is, the abnormal cell) corresponding to the existing value of the label variable Li is displayed at the center on the display screen of the monitor 5. The display example of such an entire specimen VS color image is given in FIG. 15C. By displaying the entire specimen VS color image in this way, comparison between the abnormal cell and the normal cell located around it becomes possible and the determination of the normality or abnormality of the cell by the viewer (the cytotechnologist, pathologist, etc.) is facilitated.

Also, here, the degrees of the abnormality levels determined by the system of FIG. 1, such as the determination score 147b of the abnormal cell stored in the cell region map table 130 and the values of the C/N ratio, the area of the nucleus, the luminance of the nucleus, and the luminance of the cytoplasm and their levels (I, IIa, IIb, and III) relative to the abnormal cell, may be displayed together with the image.

Moreover, the viewer may be made to clearly recognize the cell region 120 in such a way that the contour of the cell region 120 determined as the abnormality by the system of FIG. 1 is displayed in a particular color or the bounding box of the cell region 120 is blinked and displayed in a particular color. Here, when the viewer observing the entire specimen VS color image requires a more detailed observation of the abnormal cell, he performs a preset operation (for example, a push operation of Enter key of a keyboard, not shown). When the detailed observation is not required, the viewer performs a preset different operation (for example, a push operation of Space key of the keyboard).

In Step S332, a determination is made as to which operation is performed. Here, when it is determined that the operation where the more detailed observation of the abnormal cell is required is performed (namely, when the result of the determination is Yes), the process is advanced to Step S333. On the other hand, when it is determined that the operation where the detailed observation is not required is performed (namely, when the result of the determination is No), the process is advanced to Step S 335.

In Step S333, the object-of-interest three-dimensional VS image of the abnormal cell is displayed on the monitor 5. The display example of the object-of-interest three-dimensional VS image is given in FIG. 15D. In the case where the object-of-interest three-dimensional VS image is displayed on the monitor 5, when the viewer operates, for example, a keyboard or mouse device, not shown, the changeover of display to the object-of-interest three-dimensional VS image at a different focal point, a change of the display magnification of the object-of-interest three-dimensional VS image, and a change of the display field of the object-of-interest three-dimensional VS image are carried out in accordance with the contents of the operation.

After that, when the viewer requires the end of the observation, he performs a preset observation end operation (for example, the push operation of Enter key, not shown). In Step S334, a determination is made as to whether the observation end operation is performed. Here, when it is determined that the observation end operation is performed (namely, when the result of the determination is Yes), the process is advanced to Step S335. On the other hand, when it is determined that the observation end operation is not performed (namely, when the result of the determination is No), the process is returned to Step S333 so that the above procedures are repeated.

In Step S335, flag information indicating a confirmed flag is set to the confirmed flag 149 corresponding to the existing value of the label variable Li in the cell region map table 130 (FIG. 8A), and then the process of FIG. 15B is ended. By the process of Step S335, whether the viewer confirms the abnormal cell is automatically recorded through the host system 2.

The processing of the recall display of the abnormal cell mentioned above is performed as the process of Step S316 in FIG. 15A and thereby the object-of-interest three-dimensional VS image relative to the abnormal cell is displayed on the monitor 5. Also, the details of the processes extending from Step S312 to Step S320 in FIG. 15A are the same as those of the processes extending from Step S252 to Step S260 in FIG. 14 with the exception of the processes of Step S316 and Step S256. Hence, the object-of-interest three-dimensional VS images are displayed on the monitor 5 in order of increasing value of the determination score 147b relative to the abnormal cell which is the object of interest, namely, in order of the degree of the abnormality, beginning with the highest. Also, it is, of course, possible that the system is constructed so that the processing of the recall display can be immediately stopped by the operation from the viewer, not shown.

Figure 15C:
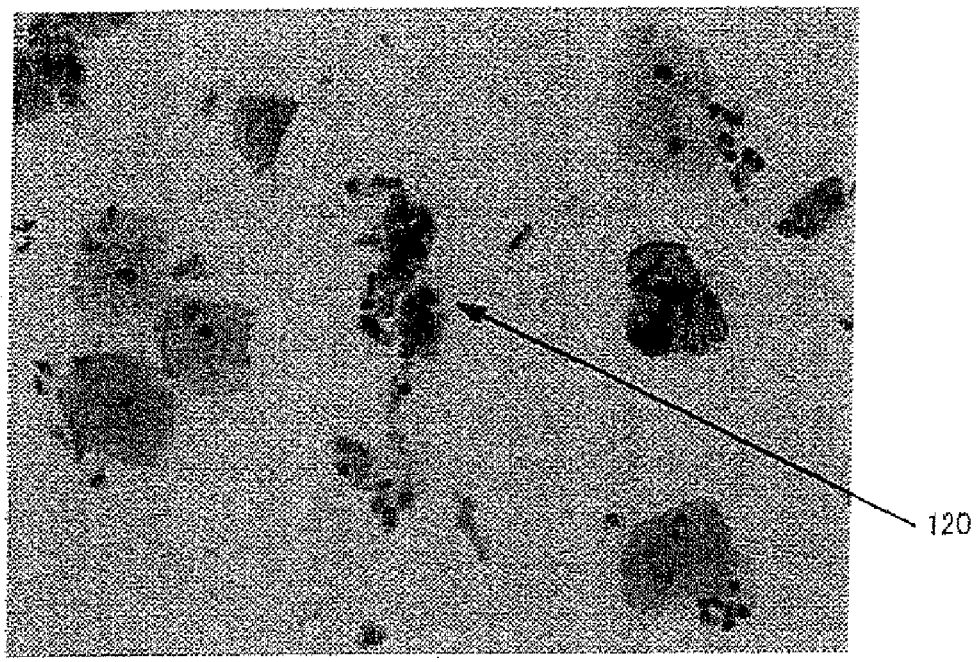
FIG. 15C is a view showing the display example of a VS color image of the entire specimen.
Figure 15D:
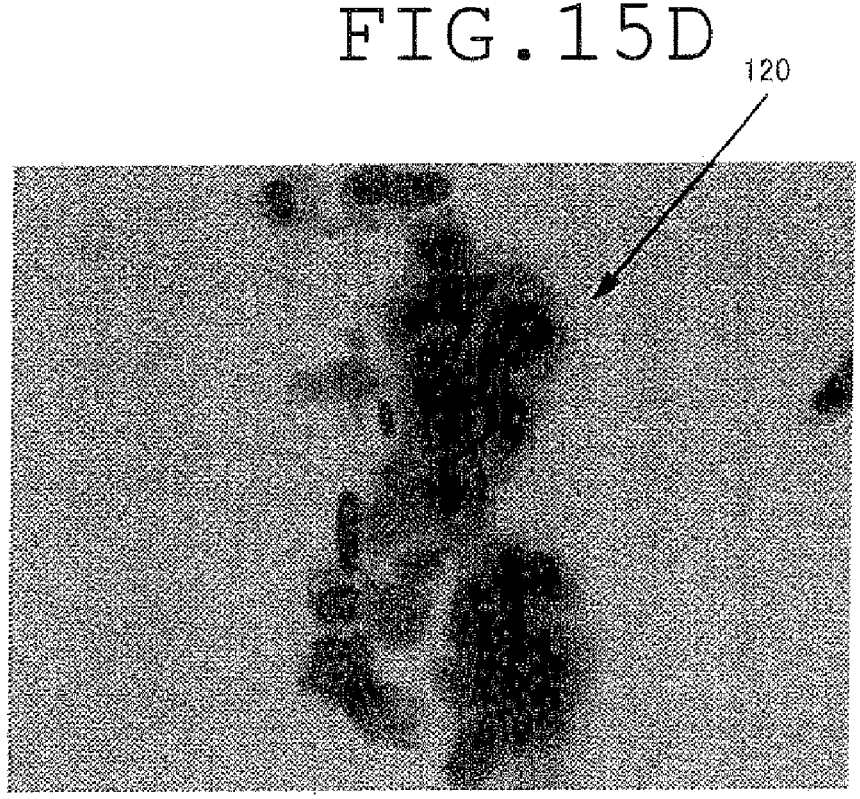
FIG. 15D is a view showing the display example of the object-of-interest three-dimensional VS image.
Figure 15E:
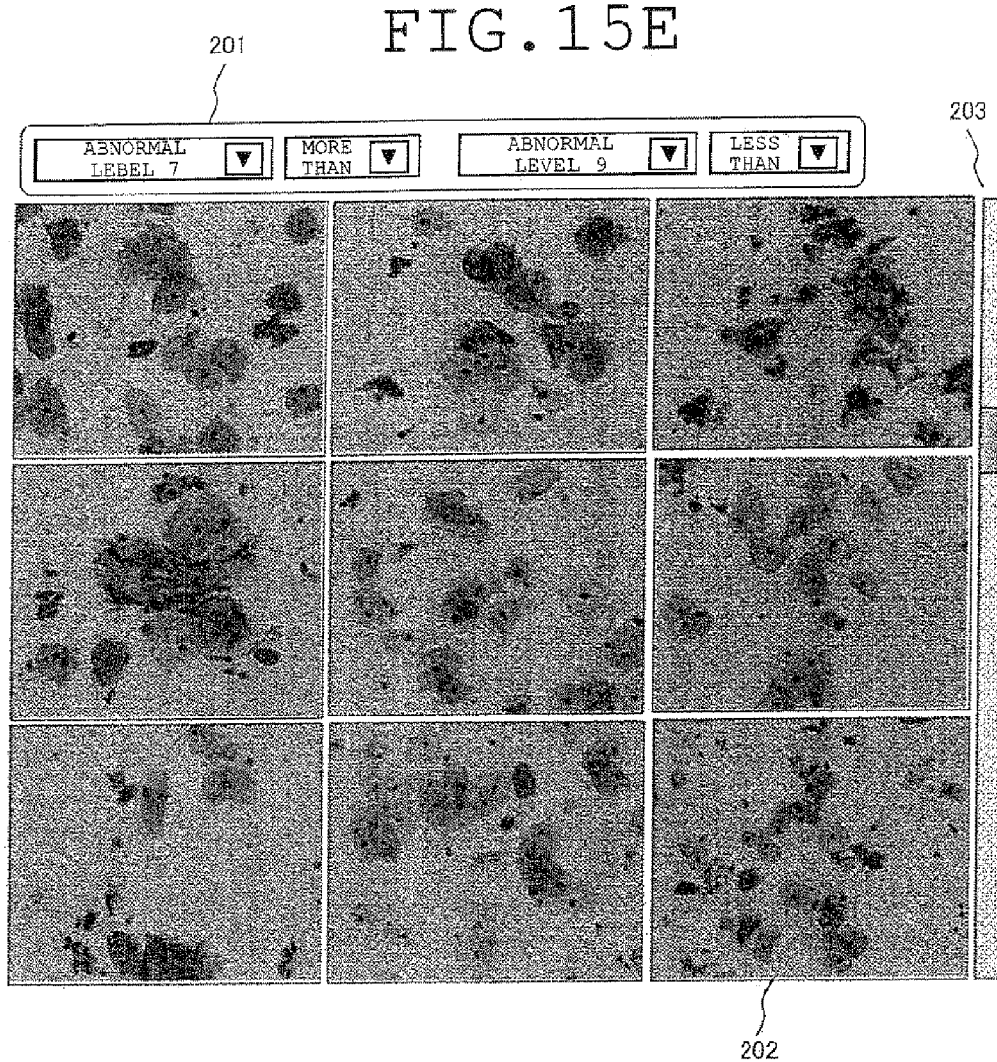
FIG. 15E is a view showing the example of recall display of the abnormal cell region.

Subsequently, a description is given of FIG. 15E. FIG. 15E shows the display example of the recall display of the abnormal cell region which is different from FIGS. 15C and 15D. In the display example of FIG. 15E, an abnormality level selection box 201, a list of thumbnail images 202 of the cell region (the thumbnail images where the image of the abnormal cell in the entire specimen VS color image is displayed at the center on the display screen), and a scroll bar 203 are displayed on the monitor 5. The abnormality level selection box 201 is provided to select the range of abnormality levels displayed as a list. Specifically, when the range of abnormality levels displayed as the list is selected by the abnormality level selection box 201, the list of the thumbnail images 202 of the cell region that the value coinciding with the range of abnormality levels selected is stored in the determination score 147b of the cell region map table 130 (FIG. 8A) is displayed in order of increasing level of abnormality (the determination score 147b). When the scroll bar 203 is moved by the drag operation of the mouse device, the list of the thumbnail images 202 is scroll-displayed. Here, when any of the thumbnail images 202 is double-clicked by the mouse device, the process shown in FIG. 15B is executed and the entire specimen VS color image and the object-of-interest three-dimensional VS image, such as those shown in FIGS. 15C and 15D, are displayed on the monitor 5.

By displaying the list of the thumbnail images 202 of the cell region as mentioned above, the viewer can observe a plurality of abnormal cell regions at a time, which is useful in the case where a general determination of the abnormal cell is made. As for the rest, it is also possible that the display is rearranged (for example, in order of increasing area or in order of darkness of the nucleus in the cell) so that the cell region map table 130 is displayed on the monitor 130 and commercial available table calculation software is used, and thereby the viewer searches out the cell region 120 in his desired order and double-clicks the corresponding row with the mouse device to make the recall display.

According to the microscope system of FIG. 1, as described above, the mistake of screening of the malignant cell is prevented without requiring a special slide glass and a particular apparatus such as a motorized microscope for observation only. Moreover, since the abnormality level of the cell is determined by the features of the nucleus and the cytoplasm and the cells can be recall-conformed with a simple operation in order of increasing level of abnormality, the accuracy and efficiency of the cytologic examination are both improved. In addition, since only the object of interest is automatically extracted as the VS image for cytology and the microscope image with high magnification is acquired with respect to the extracted object of interest to produce the three-dimensional VS image, a reduction of generation time and a decrease of the image capacity can be attained. Further, the record is automatically made as to whether the abnormal cell region is confirmed and hence a third party can be held as to whether the process of the confirmation of the abnormal cell is performed, which can be utilized for examination control.

Embodiment 2

Figure 11:
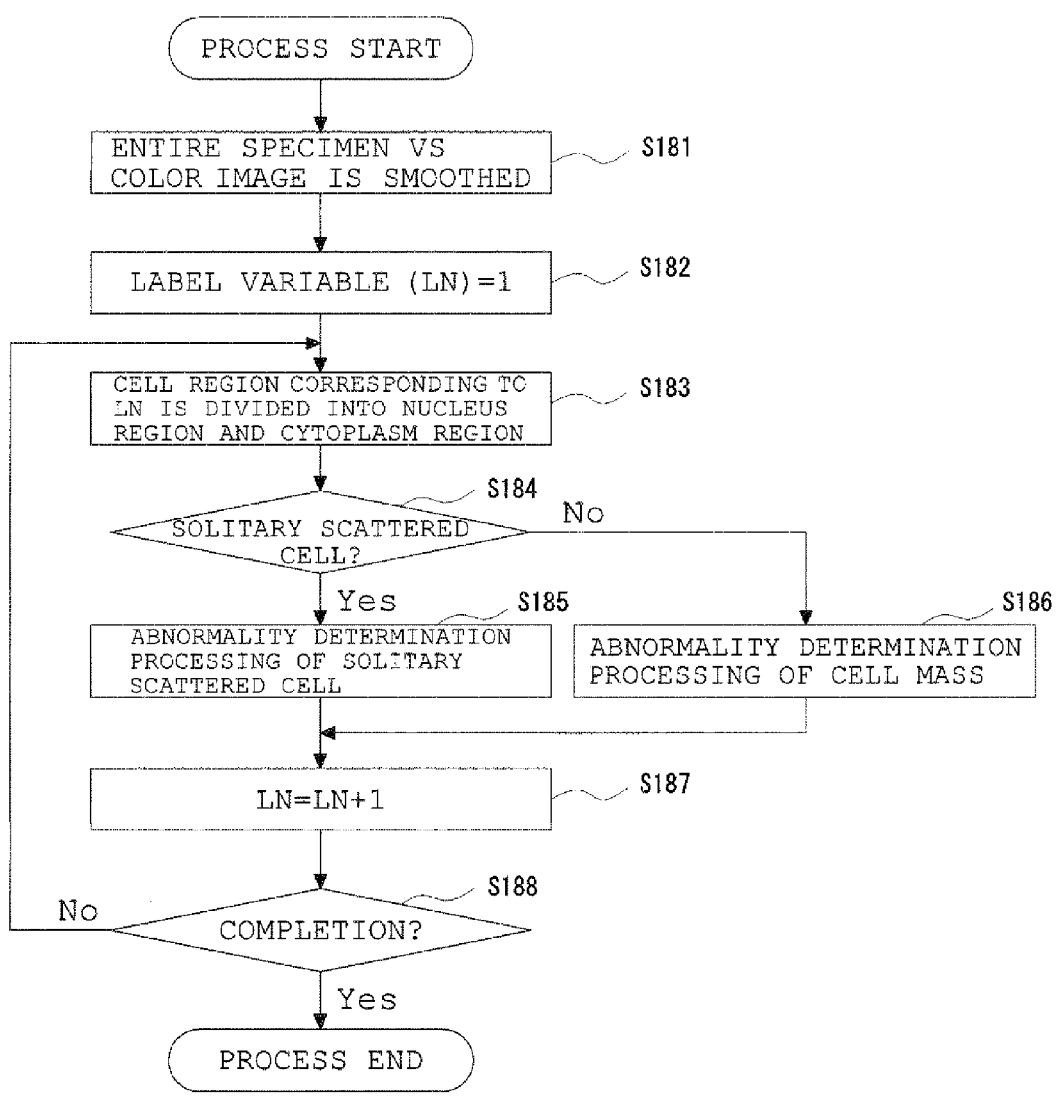
FIG. 11 is a flow chart showing the details of determination processing for normality/abnormality of the cell region.

This embodiment treats the abnormality determination processing of Steps S185 and S186 in FIG. 11, in Embodiment 1, as a primary determination processing of normality/abnormality of the cell region 120. Following this abnormality determination processing, a secondary determination processing of normality/abnormality of the cell region 120 described below is performed and thereby an attempt is made to improve the determination accuracy of normality/abnormality of the cell region 120.

Figure 16A:
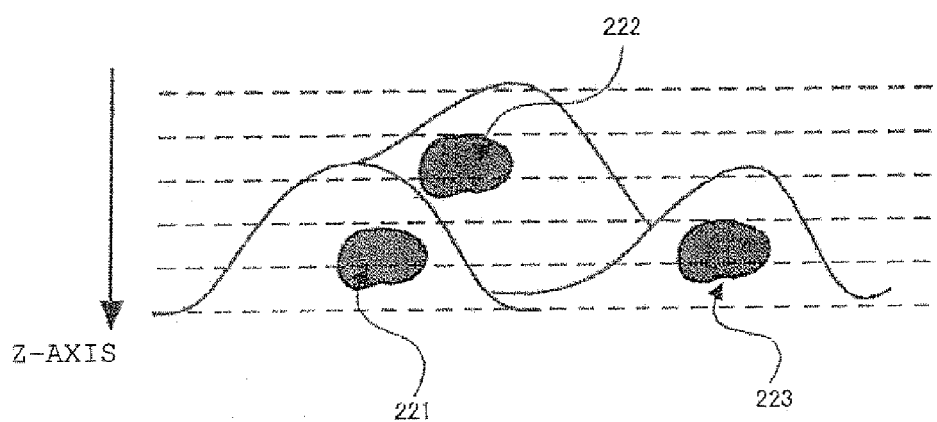
FIG. 16A is a schematic view showing a state where cells overlap in the specimen.

In the secondary determination processing, the objective lens 23 with higher magnification than that used in generating the entire specimen VS image is used, and a determination is three-dimensionally made as to whether the cell region 120 extracted by the process of Step S122 of FIG. 7 has an abnormal cell. In the following, the secondary determination processing is described with reference to FIGS. 16A-16D. FIG. 16A is a schematic view showing a state where cells overlap in the specimen 19. In this figure, it is indicated that the cells overlap in a (Z axis) direction parallel to the optical axis of the microscope apparatus 1.

Figure 16B:
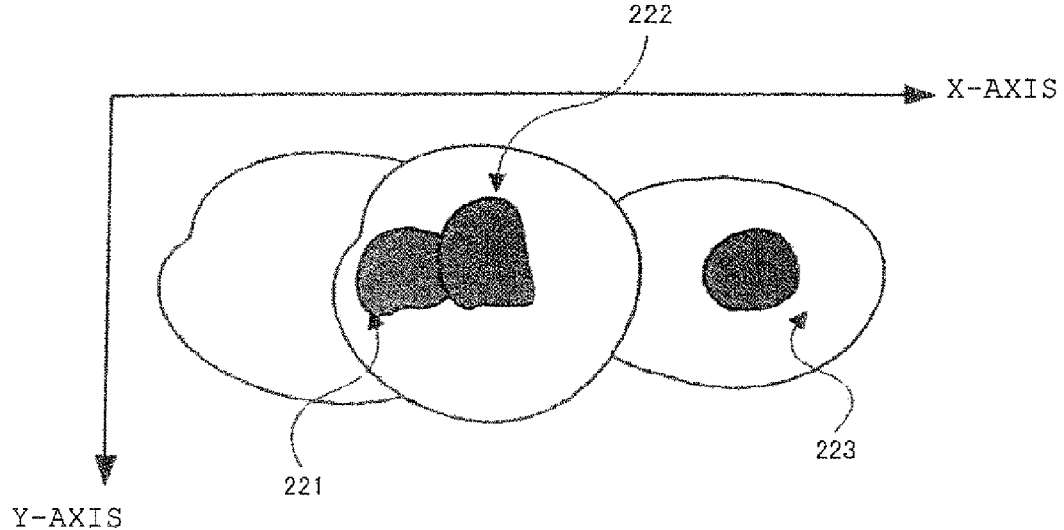
FIG. 16B is a schematic view showing the specimen of FIG. 16A, viewed from above.
Figure 16C:
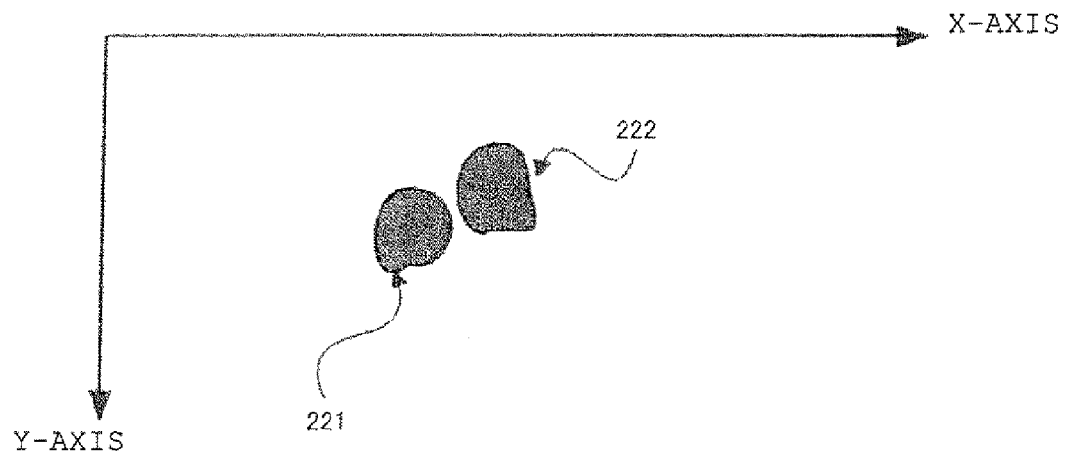
FIG. 16C is a view for explaining the separation between nuclei appearing to overlap in FIG. 16B.
Figure 16D:
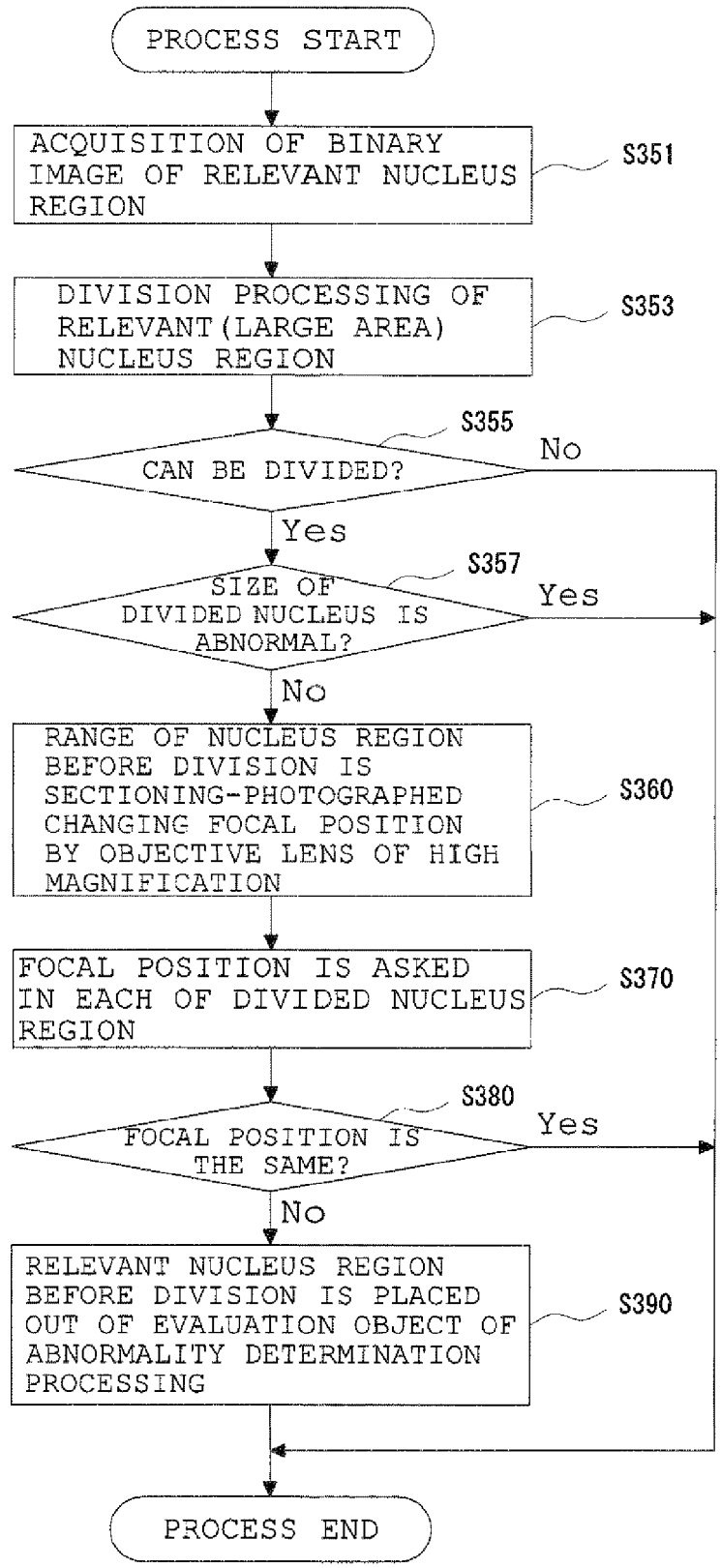
FIG. 16D is a flow chart showing the details of secondary determination processing.

FIG. 16B is a schematic view showing the specimen 19 of FIG. 16A, viewed from above. In this figure, it is indicated that, of nuclei 221, 222, and 223, the nuclei 221 and 222 overlap and are observed through overlapping of the cells. FIG. 16C is a view for explaining the separation between the nuclei overlapping and appearing in FIG. 16B. FIG. 16D is a flow chart showing the details of the secondary determination processing performed by the host system 2.

In the secondary determination processing, when it is determined that the cell region has the abnormal cell because the area of the nucleus deviates from the normal value in the primary determination processing, an erroneous determination is prevented that since the cells actually overlap and thereby the two nuclei 221 and 222 are thought of as a single nucleus, an unusually large nucleus area is observed. Also, the secondary determination processing should be executed after the abnormality determination (the primary determination) is made and its determination result is shown in the cell region map table 130 in the process of Step S185 or S186 in the normality or abnormality determination processing of the cell region of FIG. 11 and before Step S187.

The secondary determination processing is intended for only the cell region 120 which is determined and classified as "abnormality" by the primary determination processing and in which it is determined that the nucleus area registered in the map table 160 (FIG. 12D) of the nucleus region is large (the level of the "nucleus area" in the table of FIG. 13A or 13C is III).

In the following, reference is made to the details of the secondary determination processing in accordance with the flow chart shown in FIG. 16D. First, in Step S351, a process is performed for acquiring the binary image of a nucleus region (a region in which the image of the nucleus determined as a large area is represented) which is the target of the process. The region acquired by this process is hereinafter referred to as "the nucleus region". In Step S353, region dividing processing is performed with respect to the binary image of the nucleus region. For the region dividing processing performed here, well-known image processing algorithm, for example, a Watershed method or a preset times of erosion, is used.

In Step S355, a process is performed that a determination is made as to whether the binary image of the nucleus region is divided by the region dividing processing of Step S353. Here, when it is determined that the binary image is divided (a single nucleus region is divided into at least two nucleus regions) (namely, when the result of the determination is Yes), the process is advanced to Step S357. On the other hand, when it is determined that the binary image is not divided (namely, when the result of the determination is No), the process of FIG. 16D is completed, assuming that the nuclei do not overlap.

In Step S357, the area of each nucleus region after division is calculated and a determination is made as to whether the result of this calculation indicates an unusually large area to the extent corresponding to the level III in the table of FIG. 13A or 13C. Here, it is determined that the nucleus of the unusually large area is present (namely, when the result of the determination is Yes), the result of the determination that the nucleus region is abnormal remains unchanged and hence the process of FIG. 16D is completed as it is. On the other hand, when it is determined that the nucleus of the unusually large area ceases to exist (that is, when the result of the determination is No), the process is advanced to Step S360.

In Step S360, like the procedure of the process generating the object-of-interest three-dimensional VS image of Step S256 in FIG. 14, the sectioning image in which the focal position is changed, relative to the nucleus region (registered in the map table 160 of the nucleus region) before division, is photographed using the objective lens with higher magnification than that used in generating the entire specimen VS image and thereby is acquired.

In Step S370, a process is performed for determining the focal position with respect to each of nucleus regions divided by the region dividing processing of Step 353. In this process, for example, a position in each nucleus region where the luminance is lowest is decided as focal position. And, in the next Step S380, a process is performed for deciding whether the focal position decided with respect to each nucleus region is the same. In the process of this step S380, when two nuclei overlap each other as shown in FIG. 16A, the focal position is compared with respect to each of the two nuclei. On the other hand, when the nuclei more than three overlap each other, comparison of the focal position is performed by selecting, as comparison objects, two nuclei located at the position where the distance between centers of gravity of each nucleus is shortest. And when each focal position of the two nuclei is removed from each other more than a predetermined distance in the direction of Z axis (that is, when the result of the determination in Step S80 is No), it is determined that there is overlapping of nucleus and the process advanced to Step S390. On the other hand, when each focal position of the two nuclei is not removed from each other than the predetermined distance in the direction of Z axis (that is, when the result of the determination in Step S80 is Yes), it is decided that there is no overlapping of nucleus and the process of FIG. 16D is completed.

In Step S390, a process is performed that the relevant nucleus region information is deleted from the nucleus region map table 160 and then the relevant nucleus region is excluded from the object of the determination processing for normality/abnormality of the cell regions 120, and thereafter the process of FIG. 16D is completed. Also, when the contents of the nucleus region map table 160 are changed by performing the process of FIG. 16D, the processes of Steps S185 or S186 are performed again by using the geometric feature of each divided nucleus region, thereby the determination for normality/abnormality of the cell region 120 is performed, and the result of the determination is registered in the cell region map table 130 (FIG. 8A).

As described above, according to the present embodiment, as mis-detection of the abnormal cell caused by the fact that the area of the cell is evaluated to be larger than that of an actual cell because of overlapping of the cell is decreased, the examination efficiency by the viewer will be improved. Also, when the said cell region is divided into more than a predetermined number by the area dividing process, it is possible to constitute so as to stop (skip) the process of FIG. 16D by determining as over-division.

Embodiment 3

The present embodiment is designed to reduce photographing time and image capacity, etc. by stopping the photographing of sectioning image in a different focal position used a higher-magnification objective lens and the generation of the three-dimensional VS image, with respect to the cell able to determine whether it is normal or abnormal from the VS image of the entire specimen generated from the microscope images photographed by using a common objective lens. The present embodiment is described below by using FIGS. 17A to 17C and 18.

FIG. 17A is a view showing an example of an abnormality determination table of isolated and scattered cells in which the determination on the need for a detailed image is also possible. FIG. 17B is a view showing an example of an abnormality determination table of the cell mass in which the determination on the need for a detail image is also possible. The abnormality determination table shown in FIGS. 17A and 17B is designed so as to be able to select whether it is necessary to obtain the object-of-interest three-dimensional VS image, in accordance with the information of geometric features of the cell, by providing a flag 381 for indicating whether it is necessary to acquire the three-dimensional VS image, to the table of Embodiment 1 shown in FIGS. 13B and 13D, respectively. That is to say, by using this abnormality determination table, it is possible to perform such setting-up that (1) the cell region recognizable from the image of interest object in VS image of the entire specimen, the facts that, for example, a N/C ratio is high, the nucleus is bright, the area of the nucleus is large and the brightness of the cytoplasm is high, in the image of interest object in the VS image of the entire specimen, does not need to acquire the three-dimensional VS image, and that (2) the cell region in which, for example, the N/C ratio is high, the nucleus is dark and the area of the nucleus is large, needs to acquire the three-dimensional VS image of the interest object.

FIG. 17C is a view showing an example of the cell region map table in which the determination on the need for the detail image is also possible. The cell region map table 130 shown in FIG. 17C is made by adding the need flag 381 for the detail image for indicating whether or not it is necessary to obtain the three-dimensional VS image, to the cell region map table 130 in Embodiment 1 shown in FIG. 258A.

The present embodiment can be performed by partly changing the method of Embodiment 1. That is, in the Step S185 shown in FIG. 11 to perform the determination processing for normality/abnormality of the cell regions for normality or abnormality of the cell regions, and the determination processing for normality/abnormality to each of the solitary scattered cell and the cell mass in Step S186, the determination processing for normality or abnormality of the cell and the determination processing for need to acquire the three-dimensional VS image in the interest object are performed by using the abnormality determination table shown in FIGS. 17A and 17B. And, the results of both determination processings are registered as cell region information of the cell region 120 referring in the cell region map table 130 shown in FIG. 17C. Moreover, in Step S256 shown in FIG. 14, it is determined whether the formation processing of the three-dimensional VS image in the interest object should be performed on the basis of the need flag 381 for the detail image in the cell region information acquired from the cell region map table 130 of FIG. 17C. Here, when the need flag 381 for the detail image indicates "not need", the generation processing is adapted to be not performed.

Figure 18:
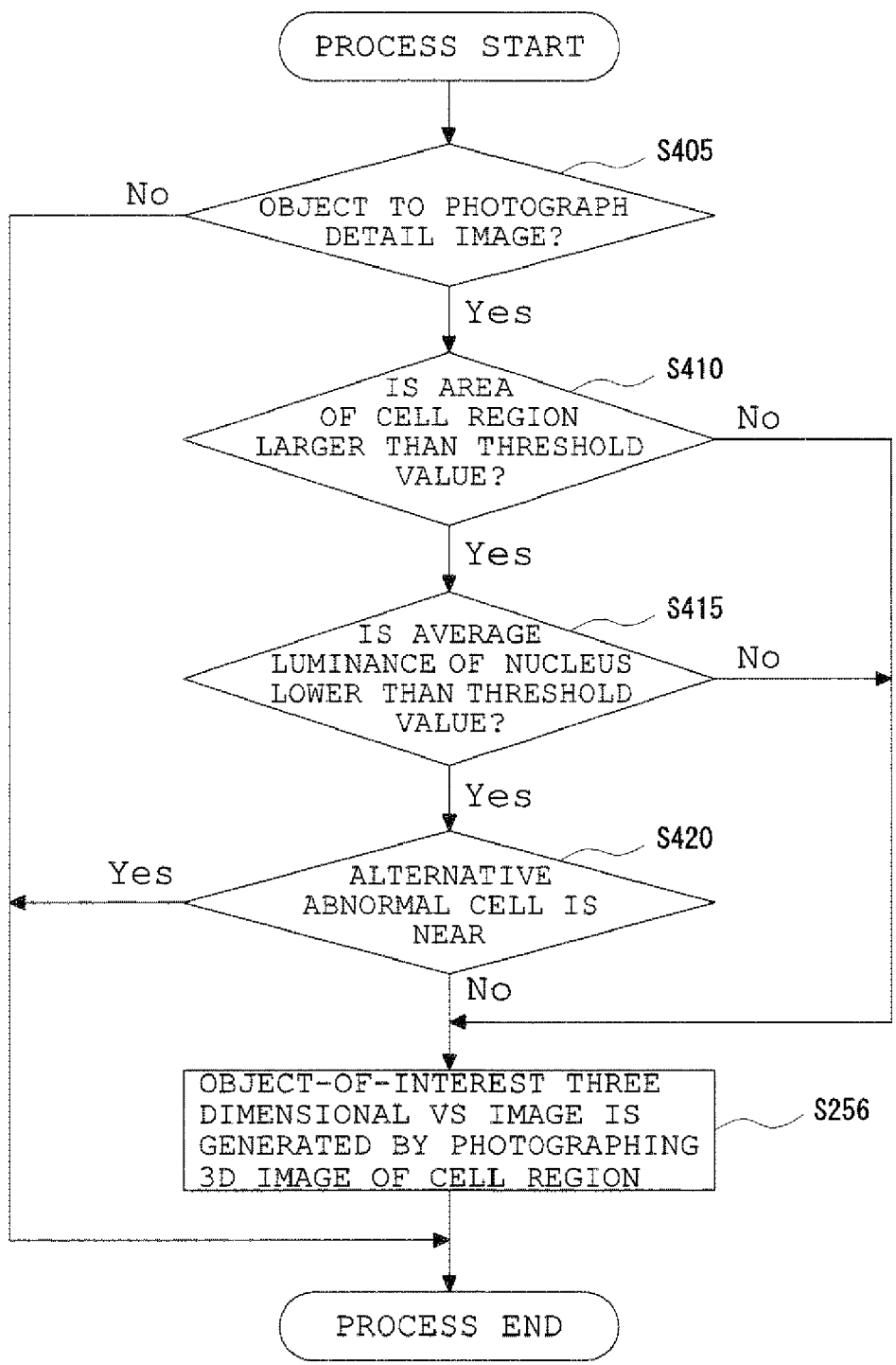
FIG. 18 is a view showing generation control processing of the object-of-interest three-dimensional VS image.

According to the above process, it becomes possible in the system of FIG. 1 to control whether the formation of the three-dimensional VS image with respect to the interest object should be performed, on the basis of degree of abnormality of the abnormal cell shown in the interest object. Moreover, it is possible to make so as not to form the three-dimensional VS image of unnecessary interest object by making so that the formation control processing of the three-dimensional VS image of the interest object is performed by the host system 2, the processing contents of which is shown by the flow chart in FIG. 18, in stead of performing as described above the processing of Step S256 shown in FIG. 14. The process shown in FIG. 18 is designed so as not to acquire the three-dimensional VS image of the interest object of the big cell mass when the three-dimensional VS image of the interest object is made so as to be able to be acquired by the method of Embodiment 1, in spite of the fact that the plural number of comparatively small abnormal cell exists in the vicinity of (within a predetermined distance from) the cell mass which is large and dark more than a predetermined value. In such cell mass, it is difficult in many cases to determine whether it is normal or abnormal. Therefore, the actual circumstances of the inspection that the abnormality is determined by the existence of the abnormal cell in the vicinity of the cell mass without determining by the image of the cell mass itself, is taken into consideration.

A process of FIG. 18 is performed instead of the process of Step S256 of FIG. 14 in the method of Embodiment 1. In the process of FIG. 18, the flag 38 of the detail image in the cell region information with respect to the cell region 120 referred in the cell region map table 130 indicates "necessity", and the process is performed to determine whether this cell region 120 is an object for acquiring the three-dimensional VS image of the interest object. Here, when the cell region 120 is determined as the object for acquiring the three-dimensional VS image of the interest object (when the result of the determination is Yes), the process is advanced to Step S410. On the contrary, when the cell region 120 is not determined as an object for acquiring the three-dimensional VS image of the interest object (when the result of the determination is No), the process of FIG. 18 is ended.

In Step S 410, a process is performed for determining whether the area of this cell region 120 is larger than a predetermined threshold value. This process is performed by, for example, referring to the information of the bounding box 132 in the cell region information with respect to this cell region 120, and determining whether the size (width and height) of this bounding box 132 is larger than a predetermined value. Here, when the area of the cell region 120 is determined to be larger than the predetermined threshold value (when the result of the determination is Yes), the process is advanced to Step S415. On the contrary, when the area of the cell region 120 is determined to be smaller than the predetermined threshold value (when the result of the determination is No), the process is advanced to Step S256.

In Step S415, the information of the brightness 144 of the nucleus with respect to this cell region 120 is referred, and the process is performed as to whether the brightness 144 of this nucleus is lower than a predetermined value. Here, when the brightness 144 of this nucleus is determined as lower than the predetermined value (when the result of the determination is Yes), the process is advanced to Step S420. On the contrary, when the brightness 144 of this nucleus is determined as higher than the predetermined value (when the result of the determination is No), the process is advanced to Step S256.

In Step S 420, a process is performed for determining whether the abnormal cell exists around (near) the cell region 120 on the basis of the cell region map table 130. In this process, for example, the number of the cell region satisfied the following three conditions is counted:

Condition 1: The abnormal cell is within a predetermined distance from a center of gravity 133 of the cell region.

Condition 2: The area of the abnormal cell is smaller than a predetermined value (the area of the level to be determined as is smaller than the threshold value in the determination processing of Step S410).

Condition 3: The abnormal cell is the object for acquiring the three-dimensional VS image of the interest object. And, when the counted value is more than the predetermined value, the determination is so performed as "the alternate abnormal cell exists near the abnormal cell" (the result of determination is Yes), and the process of FIG. 18 is ended as it is. On the contrary, when the counted value is less than the predetermined value, the determination is so performed as "the alternate abnormal cell does not exist near the abnormal cell" (the result of determination is No), and the process is advanced to Step S256. Next, in Step S256, a process is performed in the same manner as the case in FIG. 14 to form the three-dimensional VS image of the interest object, and thereafter the process of FIG. 18 is ended.

As described above, according to the present embodiment, it is possible to make so as not to perform the formation of the three-dimensional VS image of the interest object in accordance with the geometric features of the cell or the circumstances of the neighboring cell (the cell existing within the predetermined distance), and therefore it is possible to reduce the photographing time and the volume of the image file, etc.

Embodiment 4

Figure 19:
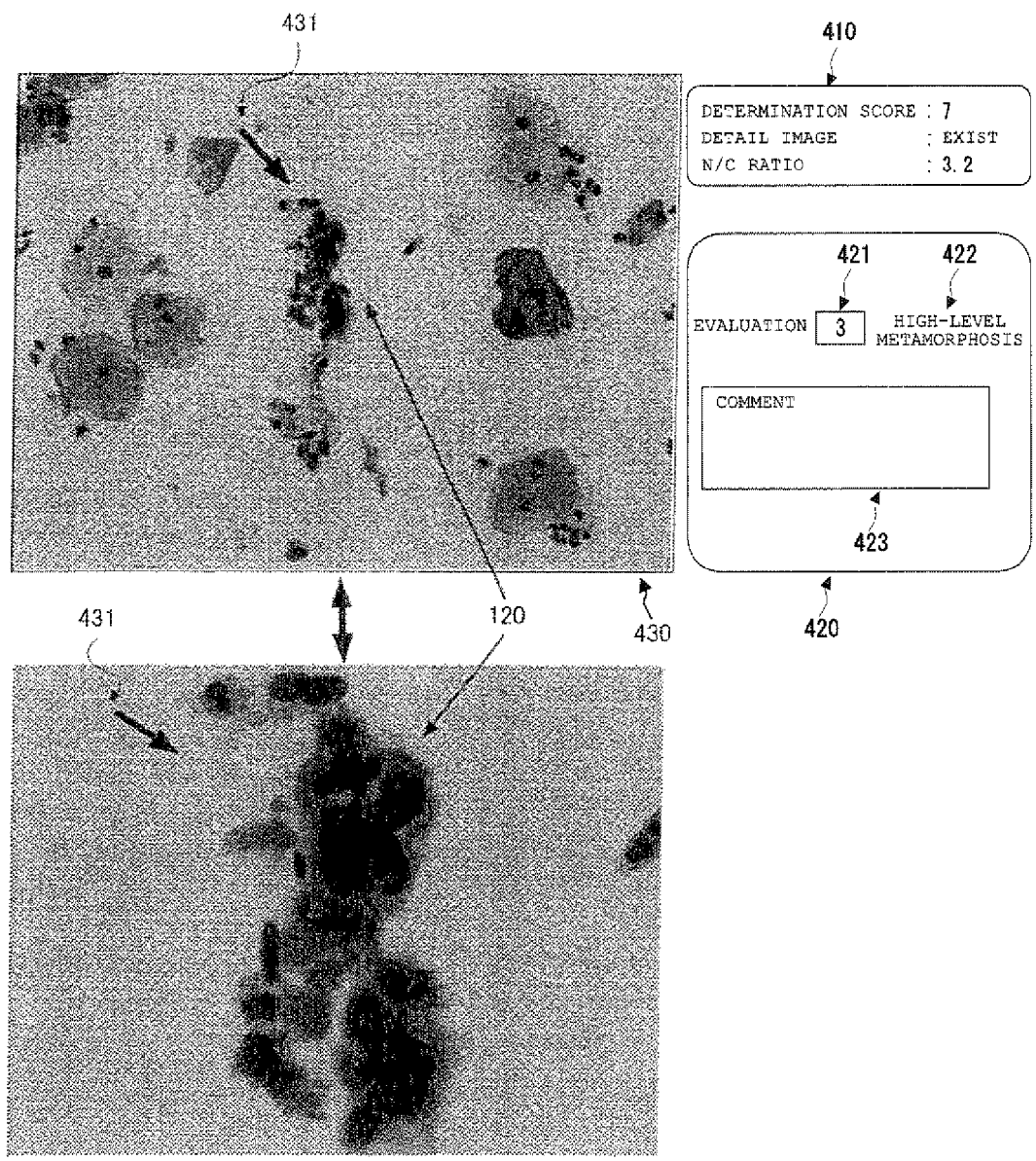
FIG. 19 is a view showing a structure example relative to the display image of the specimen.

The present embodiment is constituted to record the appraisal result of the cell and comments, etc. by the viewer and hereafter use their recorded contents, in the recall display described in Embodiment 1 as "malignant", "malignancy suspected", "degeneration", etc. FIG. 19 shows a structure example according to the present embodiment relative to the display image of the specimen 19. In FIG. 19, a VS image of the entire specimen (the VS color image of the entire specimen in Embodiment 1) is shown on an image display area 430. This display can be changed to the three-dimensional VS image of the interest object shown in the lower drawing of FIG. 19, by a predetermined operation of the viewer.

An abnormal-cell-indicating-pointer 431 indicates the interest object (the image of the abnormal cell) to be an object for observation in the VS image of the entire specimen. The registered contents of the cell region map table 130 which is the present observation object is shown in an area 410 for indicating the information of the abnormal cell.

An opinion input area 420 comprises an appraisal value input part 421, an appraisal contents display part 422 and a comment part 423. The appraisal information of the abnormal cell by the viewer is input with numerical value into the appraisal value input part 421. The meaning contents of the appraisal numerical value input in the appraisal value input part 421 is shown in the appraisal contents display part 422. FIG. 20 shows an example of a correspondence table of the appraisal numerical values and their meaning contents registered previously in the data record section 4. The comment part 423 is an input column for inputting the viewer's comments.

The host system 2 is adapted to show the three-dimensional VS image of the interest object shown in FIG. 19, instead of the VS color image of the entire specimen and the example of the three-dimensional VS image of the interest object respectively show in FIGS. 15C and 15D, by the recall display processing of the abnormal cell in question shown in FIG. 15B. And a predetermined operation performed by the viewer on the display of the picture (for example, the push-down operation of a key on the key board not shown) is detected, an input corresponding to this operation is performed to the appraisal value input part 421 and the comment part 423, and at the same time, the meaning contents corresponding to the input appraisal value take out from the correspondence table of FIG. 20 and is represented in the appraisal contents display part 422.

The input information of the appraisal numerical value of the abnormal cell and the comments acquired at this time is recorded in each column of appraisal value 502 and comment 503 of a one's opinion data table 500 as shown as an example in FIG. 21, and they are stored as a one's opinion data file in the data recorded section 4. Here, the data registered on the label 131 of the cell region map table 130 is recorded to clarify the relation between both data. Moreover, a file pass information for obtaining access to the one opinion data file is stored in the one's opinion data file information storage area not shown of the subsidiary information 61 in the VS image file 60 of the entire of specimen.

The one's opinion data input as described above is, for example, used as described below. That is, in the recall display of the abnormal cell region shown in FIG. 15E, the sample of the range designation of the above mentioned appraisal numerical value input by the viewer is possible by the abnormality level selection box 201. Here, when the range of the appraisal numerical value to be shown by a table is selected in the abnormality level selection box 201, the list of the thumbnail images 202 of the cell region that the value coinciding with the range of abnormality levels selected (the thumbnail images of the images in which the image of abnormal cell in the VS image of the entire specimen is shown at the central portion of the display scene) is shown as the appraisal value 502 in the one's opinion data table 500 in order of magnitude of the appraisal numerical value. Here, when the scroll bar 203 is moved by the drag operation of the mouse means, the list of the thumbnail images 202 is scroll-displayed.

Here, when the arbitrary thumbnail images 202 are double-click operated by the mouse means, the process shown in FIG. 15B is performed and the display scene as shown in FIG. 19 is formed, and the VS image of the entire specimen (the image which the image of abnormal cell in question is shown at the central portion of the display scene) corresponding to the thumbnail images 202 acquired by a double-click operation and the three-dimensional VS image of the interest object corresponding to the thumbnail images 202 are shown on the monitor 5 in accordance with the switching operation of the image display.

As described above, according to the present embodiment, the host system 2 acquires the input of the appraisal value relative to the interest object by the observer and determines the necessity of the three-dimensional VS image of the said interest object on the basis of the appraisal value. And the three-dimensional VS image of the interest object decided to be shown by this determination is adapted to be shown. Such process that, for example, a list of the malignant cells decide to be abnormal more than "high-level abnormity" by the viewer is browsed with the thumbnail form can be realized by the system shown in FIG. 1, and at the same time, as it is also possible to recall-display in turn abnormal images on the monitor 5, the secondary screener and the evaluation of the first screening result cell by the cytologic specialist can be performed efficiently. Moreover, for example, if such one's opinion is made so as to be recorded by each viewer, the difference between determination results by each viewer can be compared with each other in order to make possible the development of diagnose ability and the practical use for the precision control.

According to the virtual slide microscope system shown in FIG. 1 practicing the above mentioned respective embodiments, the picking-up error of malignant cells can be prevented without necessitating such specific instruments as a particular side glass and an exclusive motorized microscope, and further, the determination base of the result of the cytologic diagnosis inspection can be reserved by saving the record of the decision result of each abnormal cell. Moreover, the accuracy of the cytologic diagnosis inspection can be increased because the reasonability of the inspection result can be easily confirmed by the recall working. Additionally, a reduction of making hours and the cutting down of image volume can be performed by automatically extracting only an interesting area as VS image for cytology and by acquiring only the three-dimensional data of the interest object with higher magnification.

The embodiments of the present invention have been described in the above. However, the present invention may be improved variously within the range not deviating from the gist of the invention without limiting the respective embodiments described above.

What is claimed is:

1. A microscope system comprising
a VS image generation means for generating a virtual slide image (a VS image) of a specimen which is constructed by connecting a plurality of microscope images with a first photomagnification photographed and acquired whenever an objective lens and the specimen are moved in a direction perpendicular to the optical axis and which represents an entire image of the specimen,
an object-of-interest set means setting an object of interest with respect to the entire image of the specimen represented by the VS image, wherein the object-of-interest set means sets a region representing the image of an abnormal cell, of cells constituting the specimen in the VS image of the entire specimen, as the object of interest
and a three-dimensional VS image generation means for generating a three-dimensional VS image which is constructed by connecting the microscope images at different focal positions in accordance with said focal positions and which is constructed from the microscope images with a second photomagnification higher than the first photomagnification and represents an image of the object of interest.

2. A microscope system according to claim 1, wherein the object-of-interest set means determines whether the cell is abnormal or not, on the basis of one of the geometric feature parameter relative to the image of the cell represented by the entire specimen VS image and the image feature parameter relative to the image of the cell.

3. A microscope system according to claim 2, wherein the object-of-interest set means determines whether the cell is abnormal or not, on the basis of the areas of images of a nucleus and cytoplasm constituting the cell in the VS image and the luminances of images of the nucleus and cytoplasm.

4. A microscope system according to claim 3, wherein the object-of-interest set means discriminates that the pixels construct which of images of the nucleus and cytoplasm, on the basis of color space components of pixels constituting the image of the cell in the VS image.

5. A microscope system according to claim 1, further comprising a three-dimensional VS image display means displaying the three-dimensional VS images in a preset order when a plurality of objects of interest are set.

6. A microscope system according to claim 5, wherein the object-of-interest set means sets as the object of interest a region representing the image of an abnormal cell, of cells constituting the specimen in the VS image, and wherein the three-dimensional VS image display means displays the three-dimensional VS images relative to the object of interest in order of increasing abnormality of abnormal cells represented by the object of interest.

7. A microscope system according to claim 6, wherein the object-of-interest set means determines on the basis of one of the geometric feature parameter relative to the image of the cell represented by the VS image and the image feature parameter relative to the image of the cell, and wherein the three-dimensional VS image display means displays the three-dimensional VS images relative to the object of interest in order according to the extent of the abnormality of the cell determined by the object-of-interest set means.

8. A microscope system according to claim 7, wherein the object-of-interest set means determines the extent of the abnormality of the cell on the basis of the areas of images of a nucleus and cytoplasm constituting the cell in the VS image and the luminances of images of the nucleus and cytoplasm.

9. A microscope system according to claim 2, wherein the object-of-interest set means determines secondarily whether the cell determined to be abnormal on the basis of the VS image is abnormal or not in accordance with a plurality of microscope images with high magnification at different focal positions which are microscope images with higher magnification than the first photomagnification relative to the cell, and excludes a region representing a cell determined to be normal by this secondary determination is excluded from the setting of the object of interest.

10. A microscope system according to claim 9, wherein the object-of-interest set means determines whether the cell is abnormal or not, as the secondary determination, after the image on which the nucleus is superimposed is excluded from a criterion, when the existence of the nucleus superimposed on the image of the cell determined to be abnormal because of a large area of the image of the nucleus in the VS image is recognized on the basis of the microscope image with high magnification.

11. A microscope system according to claim 1, further comprising a VS image generation control means controlling whether the generation of the three-dimensional VS image relative to the object of interest set by the object-of-interest set means is performed by the three-dimensional VS image generation means on the basis of the extent of the abnormality of the abnormal cell represented by the object of interest.

12. A microscope system according to claim 1, further comprising a VS image generation control means controlling whether the generation of the three-dimensional VS image relative to the object of interest set by the object-of-interest set means is performed by the three-dimensional VS image generation means on the basis of the image of another cell lying within a preset distance from the abnormal cell represented by the object of interest.

13. A microscope system according to claim 1, further comprising an evaluation value acquirement means for acquiring the input of an evaluation value relative to the object of interest, a display need determination means for determining on the basis of the evaluation value relative to the object of interest as to whether the display of the three-dimensional VS image relative to the object of interest is required, and a VS image display means for displaying the object-of-interest three-dimensional VS image determined by the display need determination means to need the display.

14. An image generating method comprising
constructing a virtual slide image (a VS image) by connecting a plurality of microscope images with a first photomagnification photographed and acquired whenever an objective lens and the specimen are moved in a direction perpendicular to the optical axis and which represents an entire image of the specimen which is generated by a VS image generation means,
setting an object of interest with respect to the entire image of the specimen represented by the VS image is set by an object-of-interest set means wherein the object-of-interest is set means is operable to set a region representing the image of an abnormal cell, of cells constituting the specimen in the VS image of the entire specimen, as the object of interest, and
constructing an object-of-interest three-dimensional VS image by connecting the microscope images at different focal positions in accordance with said focal positions and which is constructed from the microscope images with a second photomagnification higher than the first photomagnification and represents an image of the object of interest of the specimen which is produced by a three-dimensional VS image generation means.

15. A non-transitory computer readable medium having a computer readable program code embodied therein, said computer readable program code adapted to be executed to implement a method for generating a report, said method comprising the steps of:
  generating a virtual slide image (a VS image) which is constructed by connecting a plurality of microscope images with a first photomagnification photographed and acquired whenever an objective lens and the specimen are moved in a direction perpendicular to the optical axis and which represents an entire image of the specimen,
  setting a region of interest with respect to the entire image of the specimen represented by the VS image, wherein the region of interest comprises an object-of-interest representing an image of an abnormal cell, of cells constituting the specimen in the VS image of the entire specimen, as the object of interest and
  generating a three-dimensional VS image which is constructed by connecting the microscope images at different focal positions in accordance with said focal positions and which is constructed from the microscope images with a second photomagnification higher than the first photomagnification and represents an image of the object of interest.

* * * * *